US012714702B2

(12) United States Patent
Gupta

(10) Patent No.: US 12,714,702 B2
(45) Date of Patent: Aug. 25, 2026

(54) COMPOSITIONS AND METHODS FOR TREATING OR PREVENTING PULMONARY HYPERTENSION

(71) Applicant: Pulmosim Therapeutics LLC, San Francisco, CA (US)

(72) Inventor: Vivek Gupta, Floral Park, NY (US)

(73) Assignee: PULMOSIM THERAPEUTICS LLC, San Francisco, CA (US)

( * ) Notice: Subject to any disclaimer, the term of this patent is extended or adjusted under 35 U.S.C. 154(b) by 460 days.

(21) Appl. No.: 18/025,563

(22) PCT Filed: Sep. 10, 2021

(86) PCT No.: PCT/US2021/049766

§ 371 (c)(1),
(2) Date: Mar. 9, 2023

(87) PCT Pub. No.: WO2022/056196

PCT Pub. Date: Mar. 17, 2022

(65) Prior Publication Data

US 2023/0330083 A1 Oct. 19, 2023

Related U.S. Application Data

(60) Provisional application No. 63/077,102, filed on Sep. 11, 2020.

(51) Int. Cl.

*A61K 31/473* (2006.01)
*A61K 45/06* (2006.01)
*A61P 9/12* (2006.01)

(52) U.S. Cl.

CPC ............ *A61K 31/473* (2013.01); *A61K 45/06* (2013.01); *A61P 9/12* (2018.01)

(58) Field of Classification Search

CPC .......... A61K 31/473; A61K 45/06; A61P 9/12
USPC .......................................................... 514/297
See application file for complete search history.

(56) References Cited

U.S. PATENT DOCUMENTS

| | | | |
|---|---|---|---|
| 2009/0226429 A1 | 9/2009 | Salcedo et al. | |
| 2011/0207711 A1 | 8/2011 | Katz et al. | |
| 2017/0240552 A1 | 8/2017 | Brown et al. | |
| 2018/0009816 A1 | 1/2018 | Buesking et al. | |
| 2023/0404995 A1* | 12/2023 | Gupta | A61P 11/00 |

FOREIGN PATENT DOCUMENTS

| | | | |
|---|---|---|---|
| CN | 106794233 A | 5/2017 |
| JP | 2003-513050 A | 4/2003 |
| JP | 2011-530607 A | 12/2011 |
| JP | 2013-528649 A | 7/2013 |
| WO | WO-2017/151886 A1 | 9/2017 |

OTHER PUBLICATIONS

Veeroju et al., PLOS ONE, Jun. 19, 2020, https://doi.org/10.1371/journal.pone.0234872 (Year: 2020).*

Orriols et al., Cell Mol Life Sci. May 23, 2017;74(16):2997 (Year: 2017).*

Andruska et al., Int. J. Mol. Sci. 2018, 19(9), 2499; https://doi.org/10.3390/ijms19092499 (Year: 2018).*

Sanna Vattulainen-Collanus, Communications Biology vol. 1, Article No. 149 (2018). (Year: 2016).*

K Hennigs Arteriosclerosis, Thrombosis, and Vascular Biology, vol. 36, (2017) NoSAuppl_1 https://doi.org/10.1161/atvb.36.suppl_1.600 (Year: 2017).*

Sanna Vattulainen-Collanus, Communications Biology vol. 1, Article No. 149 (2018). (Year: 2018).*

First Office Action & Search Report issued in Chinese Application No. 2021800738201 mailed Apr. 27, 2025 with English Translation.

Jiang et al., "The effect of Mepacrine on Acute hypoxic Pulmonary Hypertension", Fed Proc, p. 556, 1986, vol. 45.

Sobin, Sidney S., "Hypoxia and the Pulmonary Microvasculature, Physiology and Pathophysiology", CHEST, pp. 155S-156S, Mar. 1988, vol. 93, No. 3.

Xiao et al., "Inhibition of potassium channel by chronic hypoxia on pulmonary artery smooth muscle cells in rats", Chinese Journal of Tuberculosis and Respiratory Diseases, pp. 681-685, Nov. 1998, vol. 21, No. 11, English Abstract.

International Search Report and Written Opinion dated Dec. 27, 2021, PCT Application No. PCT/US2021/049766, 17 pages.

Sobin et al., "Hypoxia and the Pulmonary Microvasculature" Physiology and Pathophysiology, vol. 93, Issue 3, Mar. 1, 1988 (Mar. 1, 1988), pp. 155S-156S.

Jiang et al., Database Biosis [Online] Jan. 1, 1986 (Jan. 1, 1986), Federation Proceedings Federation Proceedings: "The Effect of Mepacrine on Acute Hypoxic Pulmonary Hypertension", XP093193088, Database accession No. PREV198631016370.

Mcshane et al., Database Biosis [Online] Jan. 1, 1987 (Jan. 1, 1987), Federation Proceedings Federation Proceedings: "Mepacrine Attenuates Oxidant Angiotensin and Potassium Chloride-Induced Pulmonary Hypertension", XP093193089, Database accession No. PREV198733017959.

Mclaughlin et al: "Contemporary Reviews in Cardiovascular Medicine—Pulmonary Arterial Hypertension", Circulation, American Heart Association, US, vol. 114, No. 13, Sep. 26, 2006 (Sep. 26, 2006), pp. 1417-1431.

Extended European Search Report (EESR) issued in EP Application No. 21867635.1 mailed Sep. 10, 2024, 7 pages.

Bonnet, S. et al., "The nuclear factor of activated T cells in pulmonary arterial hypertension can be therapeutically targeted", Proceedings of the National Academy of Sciences of the United States of America, vol. 104, No. 27, Jul. 3, 2007, pp. 11418-11423.

(Continued)

*Primary Examiner* — Kortney L. Klinkel
*Assistant Examiner* — Grace Ching Hsu
(74) *Attorney, Agent, or Firm* — Jolene S. Fernandes; Foley & Lardner LLP

(57) ABSTRACT

The present disclosure relates generally to compositions including quinacrine or pharmaceutically acceptable salts thereof and methods for using the same to prevent, ameliorate or treat pulmonary arterial hypertension and/or reducing the severity of one or more risk factors, signs, or symptoms associated with pulmonary arterial hypertension.

15 Claims, 23 Drawing Sheets

(56) References Cited

OTHER PUBLICATIONS

Chao et al., "The Protective Effect of mepacrine on acute lung edema induced by phorbol myristate acetate in rats", Chinese Journal of Physiology, vol. 33, No. 4, 1990, pp. 301-314.
Dromparis, P. et al., "Attenuating endoplasmic reticulum stress as a novel therapeutic strategy in pulmonary hypertension", Circulation, vol. 127, No. 1, Jan. 2013, pp. 115-125.
Galie, Nazzareno et al., "New horizons in pulmonary arterial hypertension therapies", European Respiratory Review, vol. 130, No. 22, 2013, pp. 503-514.
He, Y. et al., "Salubrinal attenuates right ventricular hypertrophy and dysfunctional in hypoxic pulmonary hypertension of rates", Vascular Pharmacology, vol. 87, 2016, pp. 190-198.
Hui-Li, Gan, "The Management of Acute Pulmonary Arterial Hypertension", Cardiovasc Therapeutics, vol. 29, No. 3, 2011, pp. 153-175.
Jiang, H.X. et al., "The Effect of Mepacrine on Acute Hypoxic Pulmonary Hypertension", Federation Proceedings, vol. 45, dated 1986, 2 pages.
Mclaughlin, Vallerie V. et al., "Pulmonary Aterial Hypertension", Circulation, vol. 114, 2006, pp. 1417-1431.
Mcshane et al. "Mecaprine Attenuates Oxidant Angiotensin and Potassium Chloride-Induced Pulmonary Hypertension", Federation Proceedings, 1987, 3 pages.
Muliawan, Sakti H. et al. "Trimetazidine preserves right ventricular function on pulmonary arterial hypertension patients in national cardiovascular center Harapan Kita hospital Indonesia", European Heart Journal, vol. 41, dated Jan. 13, 2020, Abstract.
Paulin, R. et al., Dehydroepiandrosterone inhibits the Src/STAT3 constitutive activation in pulmonary arterial hypertension, American Journal of Physiology-Heart and Circulatory Physiology, vol. 301, No. 5, Nov. 2011, pp. H1798-H1809.
Sobin, Sidney S., "Hypoxia and the Pulmonary Microvasculature Physiology and Pathophysiology", CHEST, vol. 93, No. 3, Mar. 1988, pp. 155S-156S.
Spiekerkoetter, E. et al., FK506 activates BMPR2, resc uses endothelial dysfunction, and reverses pulmonary hypertension, The Journal of Clinical Investigation, vol. 123, No. 8, Aug. 2013, pp. 3600-3613.
Stenmark, K. R. et al., "Animal models of pulmonary arterial hypertension: the hope for etiological discovery and pharmacological cure", American Journal of Physiology Lung Cellular and Molecular Physiology, vol. 297, No. 6, Dec. 2009, pp. L1013-L1032.
Trombetta, A. et al., "Pulmonary arterial hypertension in interferonophaties: a case report and a review of the literature", Pulmonary Circulation, vol. 9, No. 3, 2019, pp. 1-4.
Notice of Reasons for Rejection issued in Japanese Application No. 2023-516494, mailed Aug. 5, 2025.
Vitali S. H. et al: "The Sugen 5416/Hypoxia Mouse Model of Pulmonary Hypertension Revisited: Long-Term Follow-Up", Pulmonary Circulation Apr.-Jun. 2012, vol. 4,No. 4, Dec. 1, 2014 (Dec. 1, 2014), pp. 619-629. (previously submitted with Response to Non-Final Office Action on Jan. 27, 2026).
Vitali Sally H.: "CrossTalk opposing view: The mouse SuHx model is not a good model of pulmonary arterial hypertension", The Journal of Physiology, vol. 597, No. 4, Nov. 29, 2018 (Nov. 29, 2018), pp. 979-981.

* cited by examiner

FIG. 8

% E3 Ligase Inhibition 120
100
80
60
40
20
0

*

Control
PT001 (10 μM)
PT001 (20 μM)

200X Magnification

400X Magnification

FIG. 16

Medial Wall Thickness (μm)
15
10
5
0
***
SU5416/Hypoxia
PT001

COMPOSITIONS AND METHODS FOR TREATING OR PREVENTING PULMONARY HYPERTENSION

CROSS REFERENCE TO RELATED APPLICATIONS

This application is a U.S. National Stage Application under 35 U.S.C. § 371 of International Patent Application No. PCT/US2021/049766, filed Sep. 10, 2021, which claims the benefit of and priority to U.S. Provisional Appl. No. 63/077,102, filed Sep. 11, 2020, the disclosures of which are incorporated by reference herein in their entireties.

TECHNICAL FIELD

The present technology relates generally to compositions and methods for preventing, ameliorating or treating pulmonary hypertension and/or reducing the severity of one or more risk factors, signs, or symptoms associated with pulmonary hypertension.

BACKGROUND

The following description of the background of the present technology is provided simply as an aid in understanding the present technology and is not admitted to describe or constitute prior art to the present technology.

Pulmonary hypertension (PH) is a lung disorder in which mean pulmonary arterial pressure rises above normal levels (25 mm Hg at rest and 30 mm Hg during exercise). PH is classified into arterial, venous, hypoxic, thromboembolitic, and miscellaneous varieties. Of these varieties of PH, pulmonary arterial hypertension (PAH) is typically associated with the worst prognosis. PAH is subclassified as idiopathic PAH (IPAH), familial PAH (FPAH), and associated PAH (APAH) varieties. Pulmonary arterial hypertension (PAH) is a chronic and progressive disease of the lung vascular system in which endothelial dysfunction and vascular remodeling of endothelial and smooth muscle cells lead to the obstruction of pulmonary arteries, resulting in increased pulmonary vascular resistance and pulmonary arterial pressures. This leads to reduced cardiac output, right ventricular failure (cor pulmonale), and ultimately death within two to three years of diagnosis, if untreated.

In the United States, the estimated incidence and prevalence of PAH are 2.3 and 12.4 cases per million adults, respectively. PAH can develop in men and women at any age, but the disorder is nearly twice as common in females as in males. Despite recent advances in elucidating potential molecular pathways implicated in PAH and therapeutic approaches that appear to prolong survival in some PAH patients, the prognosis of PAH remains poor and there is no cure for this disorder.

SUMMARY OF THE PRESENT TECHNOLOGY

In one aspect, the present disclosure provides a method for treating or preventing pulmonary hypertension in a subject in need thereof, comprising administering to the subject a therapeutically effective amount of the composition of the present technology (i.e., quinacrine or a pharmaceutically acceptable salt thereof). In some embodiments, the subject has been diagnosed as having pulmonary arterial hypertension (PAH). In certain embodiments, the subject has been diagnosed as having an idiopathic PAH (IPAH), familial PAH (FPAH), and associated PAH (APAH). Additionally or alternatively, in some embodiments, the subject harbors a mutation selected from the group consisting of bone morphogenetic protein receptor type II (BMPR2), Serotonin (5-HTT) transporter, and Activin-Like Kinase Type-1 Receptor (ALK-1). Additionally or alternatively, in certain embodiments, the subject is a pediatric patient, a geriatric patient, an immunocompromised patient, a female patient, or a male patient, and/or is of Caucasian, South Asian, Southeastern Asian, or Middle-eastern descent. In some embodiments, the subject is human.

In any and all embodiments of the methods disclosed herein, administration of quinacrine (QA) prevents, delays the onset of, or reduces the signs or symptoms of PAH. In some embodiments, the signs or symptoms of PAH comprise one or more of persistent dyspnea on exertion, chest pain, light-headedness, exertional presyncope/syncope, palpitations, fatigue, weakness, hoarseness in the voice due to compression of the left laryngeal nerve by the dilated pulmonary artery, venous jugular distension, hepato-jugular reflux, hepatomegaly, hepatalgia, lower limb edema, ascites, generalized edema, intimal fibrosis of pulmonary arteries, increased medial thickness of pulmonary arteries, intimal hyperplasia of muscular pulmonary arteries, pulmonary artery thrombotic lesions, pulmonary arteriolar occlusion, pulmonary vascular pruning, plexiform lesions in pulmonary arteries, increased right ventricular systolic pressure, increased right ventricular hypertrophy, pulmonary vasculature hyper-proliferation, elevated serum or plasma brain natriuretic peptide (BNP) (>180 pg/mL), and elevated serum or plasma N-terminal fragment of proBNP (NT-proBNP) (≥1400 pg/mL).

Additionally or alternatively, in some embodiments, the subject exhibits a decrease in right ventricular systolic pressure (RVSP) and/or a reduction in right ventricular hypertrophy (RVH) following administration of quinacrine. Additionally or alternatively, in certain embodiments, the subject exhibits a decrease in vessel muscularization and/or a reduction in medial wall thickness in pulmonary arterioles following administration of quinacrine.

In any and all embodiments of the methods disclosed herein, QA or pharmaceutically acceptable salt thereof is administered orally, topically, intranasally, via inhalation, intrapleurally, systemically, intravenously, subcutaneously, intraperitoneally, intradermally, intraocularly, iontophoretically, transmucosally, or intramuscularly.

Additionally or alternatively, in some embodiments, the QA or pharmaceutically acceptable salt thereof is administered in an effective amount between about 1 mg/kg to about 15 mg/kg or between about 1 μM to about 10 μM. In certain embodiments, the QA or pharmaceutically acceptable salt thereof is administered in an effective amount of about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, about 10 mg/kg, about 10.5 mg/kg, about 11 mg/kg, about 11.5 mg/kg, about 12 mg/kg, about 12.5 mg/kg, about 13 mg/kg, about 13.5 mg/kg, about 14 mg/kg, about 14.5 mg/kg, or about 15 mg/kg. In some embodiments, the QA or pharmaceutically acceptable salt thereof is administered in an effective amount of about 1 μM, about 1.5 μM, about 2 μM, about 2.5 μM, about 3 μM, about 3.5 μM, about 4 μM, about 4.5 μM, about 5 μM, about 5.5 μM, about 6 μM, about 6.5 μM, about 7 μM, about 7.5 μM, about 8 μM, about 8.5 μM, about 9 μM, about 9.5 μM, or about 10 μM.

Additionally or alternatively, in some embodiments, the methods disclosed herein further comprise separately, sequentially or simultaneously administering one or more additional therapeutic agents to the subject. Examples of additional therapeutic agents include, but are not limited to, endothelin receptor antagonists (ETRAs), guanylate cyclase stimulators, prostacyclin analogues, phosphodiesterase (PDE)-5 inhibitors, dehydroepiandrosterone (DHEA), cyclosporine, tacrolimus, bestatin, imatinib, calcium-channel blockers (CCBs), dichloroacetate (DCA), trimetazidine, ranolazine, 4-phenylbutyrate, tauroursodeoxycholic acid, and salubrinal.

In some embodiments, the QA or pharmaceutically acceptable salt thereof is administered daily for 1 week, 2 weeks, 3 weeks, 4 weeks, 6 weeks, 12 weeks or more.

BRIEF DESCRIPTION OF THE DRAWINGS

FIG. 3A shows anti-proliferative efficacy of QA in human PASMC. Significant reduction in cellular hyper-proliferation was observed at Day 3 and Day 5 following single QA treatment at 3.1 and 6.2 μM. FIG. 3B shows anti-proliferative efficacy of QA in serum starved human PASMC. Significant reduction in cellular hyper-proliferation was observed at Day 5 at both 3.1 and 6.2 μM; and also at Day 3 for 6.2 μM.

FIG. 4A shows anti-proliferative efficacy of QA in high-altitude bovine PASMC. FIG. 4B shows anti-proliferative efficacy of QA in serum starved bovine PASMC. FIG. 4C shows anti-proliferative efficacy of QA in 5-hydroxytryptamine induced cellular hyper-proliferation in bovine PASMC. Data represent mean±SD (n=5) repeated over 3 experiments. *$p<0.05$.

FIG. 6A shows alterations in apoptotic induction as determined by Caspase-3 assay. FIG. 6B shows alterations in apoptotic induction as determined by Annexin V FITC assay.

FIG. 7A shows the results of lysosomal fusion with autophagosomes inhibition assay as determined by Cyto-ID® autophagy. FIG. 7B shows the results of LC3B-II expression assay as determined by Western blot analysis.

FIG. 8 demonstrates the ability of QA to directly inhibit ITCH/AIP4 E3 ligand activity as determined by ubiquitin ELISA assay. QA exhibited a dose-dependent ability to decrease overall polyubiquitination by the ITCH/AIP4 E3 ligase, with the 20 μM dose resulting in ~25% reduction in total polyubiquitination resulting from ITCH/AIP4 activity.

In FIGS. 9A-9B, PASMC were serum starved for 24 hours, and then treated with varying QA concentrations in serum-starved media. Quantification was performed using Cyto-ID® autophagy kit and Annexin-V/FITC apoptosis kit. FIG. 9A shows an increase in autophagosome accumulation as observed by fluorescence, thus demonstrating inhibition of autophagy. FIG. 9B shows relative binding of Annexin-V to phosphatidylserine on serum-starved cell membranes, thus demonstrating increased number of apoptotic cells with QA treatment. In FIG. 9C, autophagy inhibition by QA (5 μM) as depicted by increase in LC3B-II concentration in bovine high altitude PASMC quantified by western blot assay kit. Data represent mean±SD (n=3). *$p<0.05$.

FIG. 10A shows reduction in right ventricular systolic pressure (RVSP) in MCT induced rat model. FIG. 10B shows reduction in right ventricular hypertrophy (RVH) in MCT induced rat model. QA significantly reduced RVSP and RVH following disease development. Data represent mean±SEM (n=5). *$p<0.05$.

FIG. 12A shows that Ki67 and PCNA (Proliferating Cell Nuclear Antigen), two hyper-proliferation markers, have reduced expression in QA treated animal as compared to control. FIG. 12B shows that vWF (Von-Willebrand factor), or α-smooth muscle actin (α-SMA), exhibited no expression reduction in QA treated animal as compared to control. Interestingly, expression of vWF and α-SMA also did not change in MCT-induced PAH animals.

FIG. 14A shows reduction in right ventricular systolic pressure (RVSP) with QA treatment; FIG. 14B shows reduction in right ventricular hypertrophy (RVH) with QA treatment; FIG. 14C shows the degree of muscularization in pulmonary arterioles (<200 mm in diameter) with QA treatment; and FIG. 14D shows medial wall thickness in pulmonary arterioles with QA treatment. Data represent mean±SD (n=4-5). *$p<0.05$.

FIG. 16 demonstrates the effects of QA on medial wall thickness of pulmonary arteries in a SU5416/hypoxia-induced PAH animal model.

FIG. 17A shows the imagining of Ki67 and vWF. FIG. 17B shows the imagining of and PCNA and α-SMA.

FIGS. 18E-18F show western blot analysis of tissue (right lung) lysates for expression of various disease marker proteins including p62, BMPR2, LC3B-II, p21, p65, p53, phosphorylated-p53 and phosphorylated-AKT using corresponding monoclonal antibodies. Data represent mean±SD (n=3-4). $*p<0.05$.

DETAILED DESCRIPTION

Figures 1, 2:
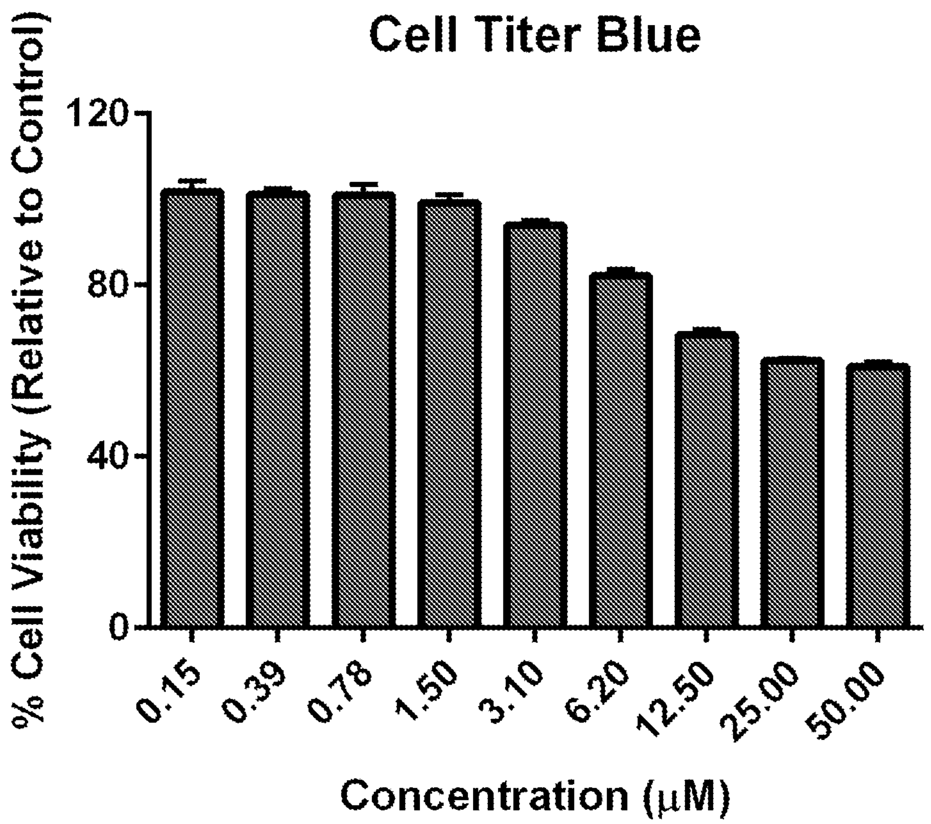
FIG. 1 the chemical structure of quinacrine (QA). As used herein, the term "PT001" also refers to QA.
FIG. 2 demonstrates the in vitro cytotoxicity effects of QA. Primary human pulmonary artery smooth muscle cells (PASMC) were treated with various concentrations (0.15-50 μM) of QA for 24 hours. Cell viability was quantified using Cell Titer Blue assay kit.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

The present disclosure provides the methods of preventing, ameliorating or treating pulmonary hypertension and/or reducing the severity of one or more risk factors, signs, or symptoms associated with pulmonary hypertension in a subject in need thereof comprising administering to the subject an effective amount of QA. Without wishing to be bound by theory, it is believed that QA acts on multiple upstream biological pathways responsible for PAH progression, including but not limited to apoptosis, autophagy, lysosomal degradation of BMPR2, and TGF-beta signaling. As demonstrated in the Examples described herein, QA (i) induces apoptosis in hyper-proliferative PASMC, thereby reducing pulmonary vasculature hyper-proliferation; (ii) is a potent inhibitor of autophagy, resulting in reduced SMC proliferation and cancer-like growth; (iii) inhibits BMPR2 degradation by blocking ubiquitination of BMPR2, and thus avoiding recognition by lysosomal machinery; and (iv) inhibits TGF-β1 expression. Accordingly, QA is useful in methods for preventing, ameliorating or treating pulmonary hypertension, in particular, PAH.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, via inhalation, intrapleurally, parenterally (intravenously, intramuscularly, intraperitoneally, or subcutaneously), rectally, intrathecally, or topically. Administration includes self-administration and the administration by another.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the terms "individual", "patient", or "subject" can be an individual organism, a vertebrate, a mammal, or a human. In some embodiments, the individual, patient or subject is a human.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing pulmonary hypertension includes preventing or delaying the initiation of pulmonary hypertension. As used herein, prevention of pulmonary hypertension also includes preventing a recurrence of one or more signs or symptoms of pulmonary hypertension.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Pulmonary Arterial Hypertension (PAH)

PAH is a progressive disorder characterized by abnormally high blood pressure (hypertension) in the pulmonary artery, the blood vessel that carries blood from the heart to the lungs. PAH is one form of a broader condition known as pulmonary hypertension (PH).

PAH is characterized by vasoconstriction, medial hypertrophy, cell proliferation and fibrosis, complex lesions (plexiform lesions), and thrombosis in situ. Pulmonary arterial changes occur in all three layers of the pulmonary artery: the tunica adventitia, tunica media, and tunica intima. Some key pathobiologic changes in PAH include vasoconstriction, arterial remodeling/inflammation, plexiform lesion, and thrombotic lesion. Vasoconstriction results in the narrowing of the lumen and tightly folded internal elastic lamina with endothelial cells pinched between the folds. Arterial remodeling and inflammation causes thickening of the adventitia and media with neointima formation due to smooth cell and fibroblast proliferation and migration, and lymphoid neogenesis. Prolonged pulmonary vasoconstriction leads to endothelial dysfunction, which is characterized by increased levels of vasoconstrictors (endothelin) and reduced production of vasodilators (nitric oxide and prostacyclin). These mechanisms have led to the development of pharmacologic agents that counteract factors involved in the pathogenesis of PAH. PAH are rare and have been associated with predisposing genetic factors such as mutations in BMPR2, 5-HTT, and Activin-Like Kinase Type-1 Receptor.

Signs and/or symptoms of PAH include, but are not limited to, persistent dyspnea on exertion, chest pain, lightheadedness, exertional presyncope/syncope, palpitations, fatigue, weakness, hoarseness in the voice due to compression of the left laryngeal nerve by the dilated pulmonary artery, venous jugular distension, hepato-jugular reflux, hepatomegaly, hepatalgia, lower limb edema, ascites, generalized edema, intimal fibrosis of pulmonary arteries, increased medial thickness of pulmonary arteries, intimal hyperplasia of muscular pulmonary arteries, pulmonary artery thrombotic lesions, pulmonary arteriolar occlusion, pulmonary vascular pruning, plexiform lesions in pulmonary arteries, increased right ventricular systolic pressure, increased right ventricular hypertrophy, pulmonary vasculature hyper-proliferation, elevated serum or plasma brain natriuretic peptide (BNP) (>180 pg/mL), and elevated serum or plasma N-terminal fragment of proBNP (NT-proBNP) (≥1400 pg/mL).

Diagnosis of PAH, which results from various pathophysiologic and hemodynamic mechanisms with nonspecific symptoms usually due to other underlying comorbid conditions, is particularly challenging, thus necessitating a stepwise approach. History and physical examination are usually evaluated first. The tests that are commonly performed to diagnose PAH and rule out other diseases are echocardiography, blood tests, pulmonary function tests, X-rays of the chest, lung blood flow scans, electrocardiography (ECG), and the "6-minute walk test", which measures how far an individual can walk in that time period. Ultimately, the majority of subjects undergo confirmation by cardiac catheterization with and without vasodilator testing.

At-Risk Populations. Individuals with multiple affected family members, who have a known BMPR2 mutation or other mutations that may cause PAH, or those with connective tissue disease (CTD) or HIV is recommended for screening by methods including Doppler echocardiography.

Physical Examination. A history of angina, dyspnea on exertion, exercise intolerance, fatigue, and syncope are among some of the signs that, although not exclusively related, can help support differential diagnosis. Upon physical examination, abnormal pulse oximetry, tricuspid regurgitation, lower-extremity edema, and signs of right-heart failure can be a few of the signs suggestive of PAH. Initially, a noninvasive test such as an echocardiograph can be performed in patients presenting with any of these signs.

Right-heart catheterization (RHC) and Vasodilator Testing. Right heart catheterization remains the standard by which the diagnosis of PAH is made. Right heart catheterization provides important prognostic information and is essential to exclude pulmonary venous hypertension by measuring the pulmonary capillary wedge pressure (PCWP). If an adequate PCWP tracing cannot be obtained, the left ventricular end-diastolic pressure should be measured. In addition, the mixed venous saturation should be sampled, and measurements of cardiac output should be obtained. The hemodynamic definition of PAH is a mean pulmonary arterial pressure (mPAP)≥25 mm Hg with a PCWP of ≤15 mm Hg and a pulmonary vascular resistance of >3 Wood units.

The degree to which mPAP and pulmonary vascular resistance can be decreased acutely by the administration of fast-acting, short-duration vasodilators reflects the extent to which vascular smooth muscle constriction is contributing to the hypertensive state. Because the vasodilator response has considerable therapeutic implications in IPAH, most patients should undergo a vasodilator trial at the time of initial cardiac catheterization. Intravenous epoprostenol, intravenous adenosine, and inhaled NO are commonly used for acute vasodilator testing. On the basis of retrospective data, the consensus definition of a positive response is defined as a reduction of mPAP by at least 10 mm Hg to a value of 40 mm Hg or less, given the observation that patients with this response are most likely to have a beneficial hemodynamic and clinical response to treatment with calcium channel blockers. Those failing to achieve this response are unlikely to improve with calcium channel blocker therapy, whereas those achieving this response may be treated with calcium channel blockers and followed up closely for both safety and efficacy of therapy. A significant vasodilator response may reflect an earlier stage of disease or a qualitatively different disease process.

Current Therapies of PAH

Current treatment options for PAH includes supportive therapy and disease-specific therapies.

Supportive Therapy

Oral anticoagulation, diuretics, oxygen, digoxin, and management of anemia may be necessary in supportive management of patients with PAH. Venous thromboembolism in certain forms of PAH is a possibility because of abnormalities in coagulation and fibrinolytic pathways along with right-heart failure and immobility. Diuretic therapy may be considered in patients with symptoms of decompensated right-heart failure resulting in fluid retention, ascites, peripheral edema, and other related symptoms. Oxygen has been shown to reduce peripheral vascular resistance, but long-term therapy has not been shown to be beneficial. Oxygen may be recommended in patients with chronic obstructive pulmonary disease, low arterial blood-oxygen pressure, evidence of symptomatic benefit, and correctable desaturation on exercise. Digoxin may improve cardiac output in IPAH and slow ventricular rate in patients with arterial tachyarrhythmias. Evidence of efficacy for chronic use in PH is lacking. Since iron deficiency is common in this population, iron supplementation can be recommended once evaluation is completed. Theoretically, IV iron replacement is usually preferred over oral therapy because oral therapy is associated with impaired absorption in these patients.

Targeted/Specific Drug Therapy

Current PAH specific therapies target components of PAH relevant molecular pathways such as voltage gated, L type calcium channels, nitric oxide cyclic guanosine monophosphate (cGMP), endothelin, and prostacyclin.

Calcium channel blockers. CCBs are indicated only in PAH patients with a documented, positive vasodilator test (e.g., responding to acute vasodilatory challenge during RHC with a drop in mPAP by between 10 and 40 mm Hg, with no drop in cardiac output). These patients are uncommon (5-10% of all cases) and have a different natural history with a five year survival rate of 90% with CCB monotherapy. Patients treated with CCBs should be closely monitored for adequate response and transitioned to PAH specific therapies if symptoms progress. Adequate long term response to CCBs in patients with APAH is rare Drugs targeting the nitric oxide pathway. Nitric oxide is a potent pulmonary vasodilator that activates soluble guanylate cyclase (sGC) to generate cGMP. cGMP causes pulmonary artery smooth muscle cell (PASMC) relaxation through cGMP dependent protein kinases, which activate downstream targets, including the large conductance, calcium sensitive potassium channel BKca. Patients with PAH have reduced lung expression of endothelial nitric oxide synthase (eNOS), which synthesizes nitric oxide, and increased expression of phosphodiesterase 5 (PDE5), which degrades cGMP to 5'-GMP. The resulting decrease in cGMP is implicated in adverse pulmonary vascular remodeling in PAH. PDE5 inhibitors and sGC stimulators augment the nitric oxide-cGMP pathway and are approved for treating PAH. A phase III trial is evaluating the safety and efficacy of long term inhaled nitric oxide in PAH (NCT02725372).

PDE5 inhibitors sildenafil and tadalafil are approved for treatment of PAH. The major side effects of PDE5 inhibitors include headache, flushing, dyspepsia, and epistaxis.

sGC stimulator riociguat directly stimulates sGC independent of nitric oxide, resulting in increased cGMP and pulmonary vasodilation. GC stimulators and PDE5 inhibitors should not be given concurrently owing to the risk of hypotension. However, transition to sGC stimulators from PDE5 inhibitors improves exercise capacity and hemodynamics in patients who have inadequate responses to PDE5 inhibitors. Headache, dizziness, hypotension, dyspepsia, and gastroesophageal reflux are the most common adverse effects of riociguat.

Endothelin receptors antagonists. Endothelin is a potent vasoconstrictor and smooth muscle mitogen. It acts through endothelin A and endothelin B receptors. Endothelin is overexpressed in the lungs and plasma of patients with PAH. The endothelial receptor antagonists (ERAs) bosentan, ambrisentan, and macitentan are beneficial in PAH. The major adverse effects of ERAs include hepatotoxicity, peripheral edema, anemia, and nasal congestion.

Drugs targeting the prostacyclin pathway. Prostacyclin and prostanoids bind prostacyclin (IP) receptors, which increases cyclic adenosine monophosphate concentrations causing non-selective pulmonary vasodilatation. They also have antiplatelet, antithrombotic, antiproliferative, and anti-inflammatory properties. Prostacyclin expression is reduced in the lungs of patients with PAH. Prostanoids include but not limited to epoprostenol, treprostinil, iloprost, and beraprost. Selexipag is an orally available, non-prostanoid activator of IP receptors.

Atrial septostomy and lung transplantation. Atrial septostomy involves the creation of a right-to-left interatrial shunt to increase cardiac output, which, despite reduction in systemic arterial oxygen saturation, may increase systemic oxygen transport, thus reducing the signs and symptoms of right heart failure. Where advanced medical therapies are available, atrial septostomy is used as a palliative measure or a bridge to lung transplantation in appropriately selected patients with refractory right heart failure or syncope/near syncope despite therapy. In regions of the world without access to current medical therapies, atrial septostomy is sometimes used as primary therapy. The procedure carries substantial risk and should only be performed by experienced operators. Lung transplantation is generally reserved for those failing the best available medical therapy. Survival in patients with PAH who undergo lung transplantation is ≈66% to 75% at 1 year. Most centers prefer double lung transplantation. Heart and lung transplantation is generally reserved for those with complex congenital heart disease.

Despite the current available treatments, the prognosis of PAH remains poor and there is no cure for this disorder. Traditional PAH therapies are limited because these conventional medications target and act on downstream pathways directly responsible for cellular functions. Such strategies only provide symptomatic relief, and are not capable of disease reversal/sustained clinical response. Moreover, the targeted downstream pathways are saturable, which generally leads to a build-up of acquired resistance and most non-responsive patients must opt for invasive lung transplantation.

Methods of Treating PAH Using the Composition of the Present Technology

In one aspect, the present disclosure provides a method for treating or preventing pulmonary hypertension in a subject in need thereof, comprising administering to the subject a therapeutically effective amount of the composition of the present technology (i.e., quinacrine or a pharmaceutically acceptable salt thereof). The chemical structure of quinacrine is shown in FIG. 1. In some embodiments, the subject has been diagnosed as having pulmonary arterial hypertension (PAH). In some embodiments, the subject has been diagnosed as having an idiopathic PAH (IPAH), familial PAH (FPAH), and associated PAH (APAH). Additionally or alternatively, in some embodiments, the subject harbors a mutation selected from the group consisting of bone morphogenetic protein receptor type II (BMPR2), Serotonin (5-HTT) transporter, and Activin-Like Kinase Type-1 Receptor (ALK-1). Additionally or alternatively, in certain embodiments, the subject is a pediatric patient, a geriatric patient, an immunocompromised patient, a female patient, or a male patient, and/or is of Caucasian, South Asian, Southeastern Asian, or Middle-eastern descent.

In any and all embodiments of the methods disclosed herein, administration of QA prevents, delays the onset of, or reduces the signs or symptoms of PAH. In some embodiments, the signs or symptoms of PAH comprise one or more of persistent dyspnea on exertion, chest pain, light-headedness, exertional presyncope/syncope, palpitations, fatigue, weakness, hoarseness in the voice due to compression of the left laryngeal nerve by the dilated pulmonary artery, venous jugular distension, hepato-jugular reflux, hepatomegaly, hepatalgia, lower limb edema, ascites, generalized edema, intimal fibrosis of pulmonary arteries, increased medial thickness of pulmonary arteries, intimal hyperplasia of muscular pulmonary arteries, pulmonary artery thrombotic lesions, pulmonary arteriolar occlusion, pulmonary vascular pruning, plexiform lesions in pulmonary arteries, increased right ventricular systolic pressure, increased right ventricular hypertrophy, pulmonary vasculature hyper-proliferation, elevated serum or plasma brain natriuretic peptide (BNP) (>180 pg/mL), and elevated serum or plasma N-terminal fragment of proBNP (NT-proBNP) (≥1400 pg/mL).

Additionally or alternatively, in some embodiments, the subject exhibits a decrease in right ventricular systolic pressure (RVSP) and/or a reduction in right ventricular hypertrophy (RVH) following administration of quinacrine. RVSP is generally determined using right heart catheterization (see supra), which is known to a skilled in the art. In some embodiments, the subject exhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% reduction in RVSP following administration of quinacrine. In certain embodiments, the subject exhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% reduction in RVH following administration of quinacrine.

Additionally or alternatively, the subject exhibits a decrease in vessel muscularization and/or a reduction in medial wall thickness in pulmonary arterioles following administration of quinacrine. In some embodiments, the subject exhibits at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 310%, at least 320%, at least 330%, at least 340%, at least 350%, at least 360%, at least 370%, at least 380%, at least 390%, at least 400% reduction in the medial wall thickness following administration of quinacrine.

Additionally or alternatively, the subject exhibits decreased expression of hyper-proliferating biomarkers such as Ki67, Proliferating Cell Nuclear Antigen (PCNA), and serpinel following administration of QA. Additionally or alternatively, the subject exhibits reduced expression of IL-6, and/or Acta2 following administration of QA.

Additionally or alternatively, in some embodiments, the methods of the present technology further comprise separately, sequentially or simultaneously administering one or more additional therapeutic agents to the subject. In some embodiments, the additional therapeutic agents are selected from the group consisting of: endothelin receptor antagonists (ETRAs), guanylate cyclase stimulators, prostacyclin analogues, phosphodiesterase (PDE)-5 inhibitors, dehydroepiandrosterone (DHEA), cyclosporine, tacrolimus, bestatin, imatinib, calcium-channel blockers (CCBs), dichloroacetate (DCA), trimetazidine, ranolazine, 4-phenylbutyrate, tauroursodeoxycholic acid, and salubrinal.

In any embodiments of the methods disclosed herein, the subject may be a human.

Modes of Administration and Effective Dosages

Any method known to those in the art for contacting a cell, organ or tissue with QA may be employed. Suitable methods include in vitro, ex vivo, or in vivo methods. In vivo methods typically include the administration of QA or pharmaceutically acceptable salt thereof to a mammal, suitably a human. When used in vivo for therapy, QA or pharmaceutically acceptable salt thereof is administered to the subject in effective amounts (i.e., amounts that have desired therapeutic effect). The dose and dosage regimen will depend upon the degree of the disease state of the subject, the characteristics of the particular composition used, e.g., its therapeutic index, the subject, and the subject's history.

The effective amount may be determined during preclinical trials and clinical trials by methods familiar to physicians and clinicians. An effective amount of QA or pharmaceutically acceptable salt thereof useful in the methods may be administered to a mammal in need thereof by any of a number of well-known methods for administering pharmaceutical compositions. The composition including QA or pharmaceutically acceptable salt thereof may be administered systemically or locally. In any and all embodiments of the methods disclosed herein, QA or pharmaceutically acceptable salt thereof is administered orally, topically, intranasally, via inhalation, intrapleurally, systemically, intravenously, subcutaneously, intraperitoneally, intradermally, intraocularly, iontophoretically, transmucosally, or intramuscularly.

QA may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compositions that are not intended for administration to a patient. Pharmaceutically acceptable salts can be derived from pharmaceutically acceptable inorganic or organic bases and from pharmaceutically acceptable inorganic or organic acids. In addition, when a composition contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration.

The composition described herein, or a pharmaceutically acceptable salt thereof, can be incorporated into pharmaceutical compositions for administration, singly or in combination, to a subject for the treatment or prevention of PAH described herein. Such compositions typically include the active agent and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compositions can also be incorporated into the compositions.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit high therapeutic indices are advantageous. While compositions that exhibit toxic side effects may be used, care should be taken to design a delivery system that targets such compositions to the site of affected tissue in order to minimize potential damage to uninfected cells and, thereby, reduce side effects.

The data obtained from the cell culture assays and animal studies can be used in formulating a range of dosage for use in humans. The dosage of such compositions may be within a range of circulating concentrations that include the ED50 with little or no toxicity. The dosage may vary within this range depending upon the dosage form employed and the route of administration utilized. For any composition used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

Typically, an effective amount of the composition, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the composition ranges from 0.001-10,000 micrograms per kg body weight. In one embodiment, composition concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of a composition may be defined as a concentration of the composition at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

For therapeutic and/or prophylactic applications, a composition comprising QA or pharmaceutically acceptable salt thereof, is administered to the subject. In some embodiments, the QA or pharmaceutically acceptable salt thereof is administered in an effective amount between about 1 mg/kg to about 15 mg/kg. In certain embodiments, the QA or pharmaceutically acceptable salt thereof is administered in an effective amount of about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, about 10 mg/kg, about 10.5 mg/kg, about 11 mg/kg, about 11.5 mg/kg, about 12 mg/kg, about 12.5 mg/kg, about 13 mg/kg, about 13.5 mg/kg, about 14 mg/kg, about 14.5 mg/kg, or about 15 mg/kg. Additionally or alternatively, in some embodiments, the QA or pharmaceutically acceptable salt thereof is administered in an effective amount between about 1 μM to about 10 μM. In certain embodiments, the QA or pharmaceutically acceptable salt thereof is administered in an effective amount of about 1 μM, about 1.5 μM, about 2 μM, about 2.5 μM, about 3 μM, about 3.5 μM, about 4 μM, about 4.5 μM, about 5 μM, about 5.5 μM, about 6 μM, about 6.5 μM, about 7 μM, about 7.5 μM, about 8 μM, about 8.5 μM, about 9 μM, about 9.5 μM, or about 10 μM. Values and ranges intermediate to the recited values are also contemplated as part of the present disclosure.

In some embodiments, the QA or pharmaceutically acceptable salt thereof is administered one, two, three, four, or five times per day. In some embodiments, the QA or pharmaceutically acceptable salt thereof is administered more than five times per day. Additionally or alternatively, in some embodiments, the QA or pharmaceutically acceptable salt thereof is administered every day, every other day, every third day, every fourth day, every fifth day, or every sixth day. In some embodiments, the QA or pharmaceutically acceptable salt thereof is administered weekly, bi-weekly, tri-weekly, or monthly. In some embodiments, the QA or pharmaceutically acceptable salt thereof is administered for a period of one, two, three, four, or five weeks. In some embodiments, the QA or pharmaceutically acceptable salt thereof is administered for six weeks or more. In some embodiments, the QA or pharmaceutically acceptable salt thereof is administered for twelve weeks or more. In some embodiments, the QA or pharmaceutically acceptable salt thereof is administered for a period of less than one year. In some embodiments, the QA or pharmaceutically acceptable salt thereof is administered for a period of more than one year. In some embodiments, the QA or pharmaceutically acceptable salt thereof is administered throughout the subject's life.

In some embodiments, the QA or pharmaceutically acceptable salt thereof is administered daily for 1 week or more. In some embodiments of the methods of the present technology, the QA or pharmaceutically acceptable salt thereof is administered daily for 2 weeks or more. In some embodiments of the methods of the present technology, the QA or pharmaceutically acceptable salt thereof is administered daily for 3 weeks or more. In some embodiments of the methods of the present technology, the QA or pharmaceutically acceptable salt thereof is administered daily for 4 weeks or more. In some embodiments of the methods of the present technology, the QA or pharmaceutically acceptable salt thereof is administered daily for 6 weeks or more. In some embodiments of the methods of the present technology, the QA or pharmaceutically acceptable salt thereof is administered daily for 12 weeks or more. In some embodiments, the QA or pharmaceutically acceptable salt thereof is administered daily throughout the subject's life. Values and ranges intermediate to the recited values are also contemplated as part of the present disclosure.

EXAMPLES

The present technology is further illustrated by the following Examples, which should not be construed as limiting in any way.

Example 1: Methods and Materials

Primary human PASMC were isolated from PAH patients. For these experiments, specifically human PASMC from SMC II (Patient ID: L164) obtained from Pulmonary Hypertension Breakthrough Initiative (PHBI) were used.

Cytotoxicity

Cytotoxicity analysis for QA on diseased IPAH SMC II (Patient ID: L164) cells was carried out using CellTiter-Blue® Cell Viability Assay (Promega, Madison, WI, USA). Briefly, upon 90% confluency, SMC II cells were harvested and seeded in TC-treated 96-well plates at a density of 2500 cells/well and were allowed to adhere overnight. Following day, cells were treated with varying concentrations of QA (0.15-50-μM). Cell viability was measured after 24 hours following the manufacturer's protocol. Briefly, 20 μL of CellTiter-Blue® assay reagent was added to treatment wells and plates were incubated at 37° C./5% $CO_2$ for two hours followed by evaluation of fluorescence at 540 ex/590 em. % Cell viability for each treatment group was calculated relative to the control untreated group of cells. Data was averaged from n=6 for SMC II.

Standard Cell Proliferation

Cellular proliferation for diseased IPAH SMC II (Patient ID: L164) cells was evaluated using CyQUANT™ Direct Cell Proliferation Assay (ThermoFisher Scientific, Waltham, MA, USA). Briefly, upon 90% confluency, SMCs were harvested and seeded in TC-treated 96-well plates at a density of 1000 cells/well and were allowed to adhere overnight.

Human or bovine PASMC were treated with varying concentrations of QA (1.5-, 3.1-, and 6.2-μM). Cellular proliferation was measured at day 1, day 3 and day 5 by following the manufacturer's protocol. Briefly, a reagent mix of nucleic acid stain and background suppressor were added in PBS followed by addition of the mix in treatment wells (100 μL/well). The plates were incubated at 37° C./5% $CO_2$ for one hour followed by evaluation of fluorescence at 485 ex/535 em. Proliferation inhibition was analyzed relative to control wells on each time point. Data was averaged from two trials with n=6 for SMC II and one trial of n=4 for SMC III.

Proliferation after Cell Starvation

Briefly, diseased IPAH SMC II cells were seeded in TC-treated 96 well plates in FBS-rich medium and were allowed to adhere overnight. Following day, FBS-rich media was replaced with FBS-Starved media (0% FBS). Cells were further incubated at 37° C./5% $CO_2$ for 24 hours followed by treatments with varying concentrations of QA (1.5-, 3.1-, and 6.2-μM) with dilutions being made in FBS-Starved media. Cellular proliferation was measured as described herein.

Cellular Uptake

Cellular uptake studies were performed to visualize the internalization of QA in diseased IPAH SMC-II cells. This study demonstrates QA's ability to traverse across the cell membrane primarily via passive diffusion. Briefly, SMC-II cells were trypsinized and seeded in TC-treated 8-chambered cover glass (Eppendorf, Hauppauge, NY, USA) (10,000 cells/chamber). Cells were incubated and allowed to attach and grow overnight. Following day, growth medium was aspirated, and cells were treated with QA (5- and 10-μM) followed by incubation at 37° C./5% $CO_2$ for 3-hours. Further, cells were fixed using 4% paraformaldehyde (PFA) for 10 minutes. PFA was then aspirated, and the chambers were washed with ice-cold PBS 3 times. Next, chamber from the cover glass was carefully removed. Microscopic slide was prepared by placing vectashield hard-set mounting medium with DAPI (Vector Laboratories, Burlingame, CA, USA), followed by carefully inverting the cover glass over slide, to avoid bubble formation. The slide was then allowed to sit overnight at 4° C. to harden the mounting medium. Cells were then imaged using an EVOS-FL (Thermo Scientific, Waltham, MA, USA) fluorescence cell imaging system using a 20× magnification lens.

Caspase-3 Assay

Once it was established that QA successfully inhibits hyperproliferation in diseased patient-derived PASMCs, SMC-II cells were used for further analysis on molecular markers and pathways to identify the potential mechanism of action of this repurposed molecule. Caspase-3 level in SMC II cells was evaluated using EnzCheck™ Caspase-3 assay kit (ThermoFisher Scientific, Waltham, MA, USA) following the manufacturer's protocol. Briefly, upon 90% confluency, SMC II cells were harvested and seeded in 100 mm TC treated culture dishes at a density of 250,000 cells/well and allowed to adhere overnight. Following day, cells were treated with QA (5- and 10-μM) for 6 hours followed by harvesting. Harvested cells were lysed using a lysis buffer for 30 minutes on ice. The cells were centrifuged, and supernatant was used to analyze levels of a caspase-3 substrate aminomethylcoumarin (AMC)-derived substrate Z-DEVD-AMC (fluorescence measurement at 360 ex/460 em).

Annexin V Assay

Bovine PASMC were serum starved in FBS-free media for 24 hours, and then treated with QA for 24 hours at various concentrations (0, 2.5, or 5 μM). Annexin V levels were measured with Annexin V FITC assay kit (#600300, Cayman Chemical, Ann Arbor, MI) according to manufacturer's manual.

Autophagy Inhibition Assay

Bovine PASMCs were serum starved in FBS-free media for 24 hours, and then treated with QA for 24 hours at various concentrations (0, 2.5, or 5 μM). Autophagic inhibition (lysosomal fusion with autophagosomes) was measured with Cyto-ID® autophagy detection kit (Enzo Lifesciences Inc., Farmingdale NY) according to manufacturer's manual.

Autophagy Inhibition Assay (LC3B-II Expression)

High-altitude bovine PASMCs were used to determine the effect of QA on LC3B-II, an autophagy marker, by western blotting (#3868S, LC3B (D11) XP Rabbit monoclonal antibody, Cell Signaling, Danvers, MA).

ITCH/AIP E3 Ligand Activity Assay

To evaluate the ability of QA to directly inhibit ITCH/AIP4 E3 ligand activity, a ubiquitin ELISA kit UbiQuant™ (Life Sensors, Malvern, PA) was used according to manufacturer's manual. The ligand activity inhibition by QA at multiple concentrations (0, 10, or 20 μM) in presence of ubiquitin was quantified.

Trichrome Staining for Visualization of Pulmonary Arteries and Evaluation of Medial Wall Thickness At the end of treatment period with QA, animals were sacrificed. Chest was surgically opened to expose rat lungs. Lung tissues were collected, and blinded tissues were sectioned by Reveal Bio (San Diego, CA) at 5 μm thickness. 2 tissue sections for each animal were earmarked for Trichrome staining; and 8 more sections were provided blank for custom staining.

Tissue sections were stained using trichrome staining to visualize pulmonary arteries for all treatment and control groups. Stained lung sections were imaged using Zeiss Axio Scope A1 microscope equipped with Axiocam 506 color camera and Zeiss Zen 2.3 software. Medial wall thickness for similar sized pulmonary arteries was measured using a Motic BA210 microscope and measurements were made using Motic Image plus 2.0 software. Five pulmonary artery walls were analyzed per animal (n=2 to 5)

Immunofluorescence for MCT Models

Preclinical in-vivo studies for QA were earlier performed at a dose of 10 mg/kg once-a-day in monocrotaline (MCT) induced therapeutic PAH model. Hemodynamic parameters were collected and lung tissues were also collected and were sectioned for visualizing the impact of QA treatment on various PAH biomarkers in-vivo.

OCT compound embedded Tissue sections for control animals, MCT induced PAH animals and QA treated animals were further subjected to immunofluorescent staining to analyze expression levels of essential molecular markers. Briefly, tissue sections were washed twice with 1×PBS followed by blocking for one hour using a blocking buffer (Cell Signaling Technology, Danvers, MA, USA). Followed by blocking, tissue sections were stained with respective primary antibodies overnight; VWF #ab15419, 1:100 (abcam), α-SMA #489385, 1:500 (CST), Ki67 #9129S (CST), 1:250 and PCNA #2586S (CST), 1:100. Following day, tissue sections were washed with 1×PBS twice followed by incubation with Anti-rabbit IgG (H+L), F(ab')2 Fragment (Alexa Fluor® 488 Conjugate) #4412S 1:250 (CST) and Anti-mouse IgG (H+L), F(ab')2 Fragment (Alexa Fluor® 594 Conjugate) #8890S, 1:500 (CST) for one hour. Further, sections were washed with 1×PBS twice and the nuclei were stained with DAPI using Vectashield hardset antifade mounting medium with DAPI (Vector Laboratories, Burlingame, CA, USA). Tissues were imaged using Zeiss Axioplan 2 fluorescence microscope (Carl Zeiss AG, Jena, Germany).

Immunofluorescence for Hypoxia Models

Preclinical in-vivo studies for QA were earlier performed at a dose of 10 mg/kg once-a-day in a SU5416/Hypoxia-induced preventative/prophylactic PAH model. Hemodynamic parameters were collected and lung tissues were also collected and were sectioned for visualizing the impact of QA treatment on various PAH biomarkers in-vivo.

Paraffin embedded tissue sections for control animals, hypoxia induced PAH animals and QA treated animals were further subjected to immunofluorescent staining to analyze expression levels of essential molecular markers. Deparaffinization of tissues was done by exposing tissue sections to a solution of xylene for 3 minutes twice followed by washing with 200 proof absolute 99.8% ethanol and 50% ethanol. Tissues were further washed with 1×PBS twice to ensure complete deparaffinization. Similar protocol was followed hereon for immunofluorescent staining of tissue sections.

Example 2: OA Ameliorates PH Associated Cellular Hyper-Proliferation In-Vitro in Primary Pulmonary Artery Smooth Muscle Cells (PASMC)

First, in vitro cytotoxicity of QA on primary human PASMC was performed using Cell Titer Blue assay kit. >85% viability was observed at up to 6.2 μM QA concentration, thus it is considered safe at 6.2 μM and lower concentrations (FIG. 2). Cytotoxicity of QA in bovine HAPASMC was also tested for up to 48 hours with cell viabilities >90%, thus demonstrating the safety of the drug on normal cells (data not shown).

Figure 3A:
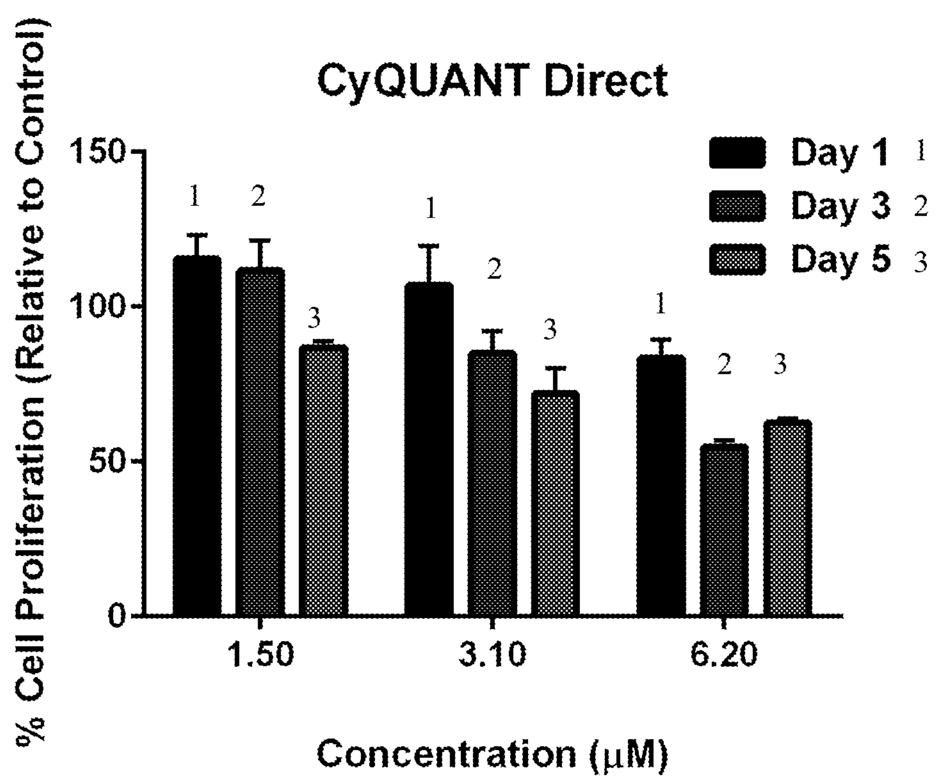
FIGS. 3A-3B demonstrate concentration-dependent anti-proliferative efficacy of QA in primary human PASMC. Primary human PASMC were treated with QA up to 6.2 μM concentration. Cell proliferation was quantified by Cyquant Direct.
Figure 3B:
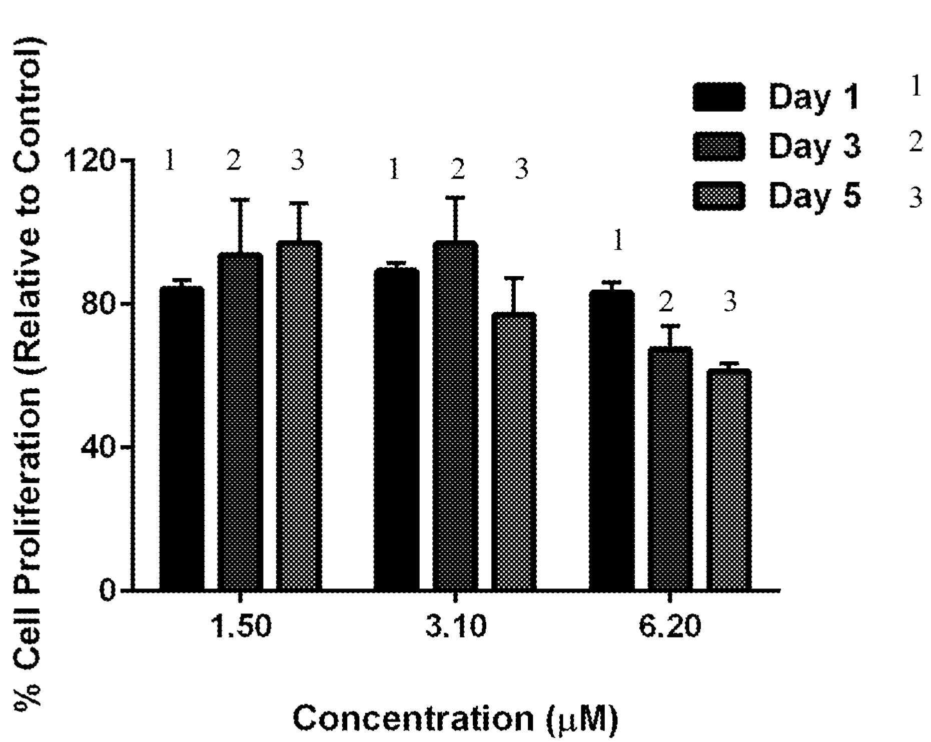
Figure 4A:
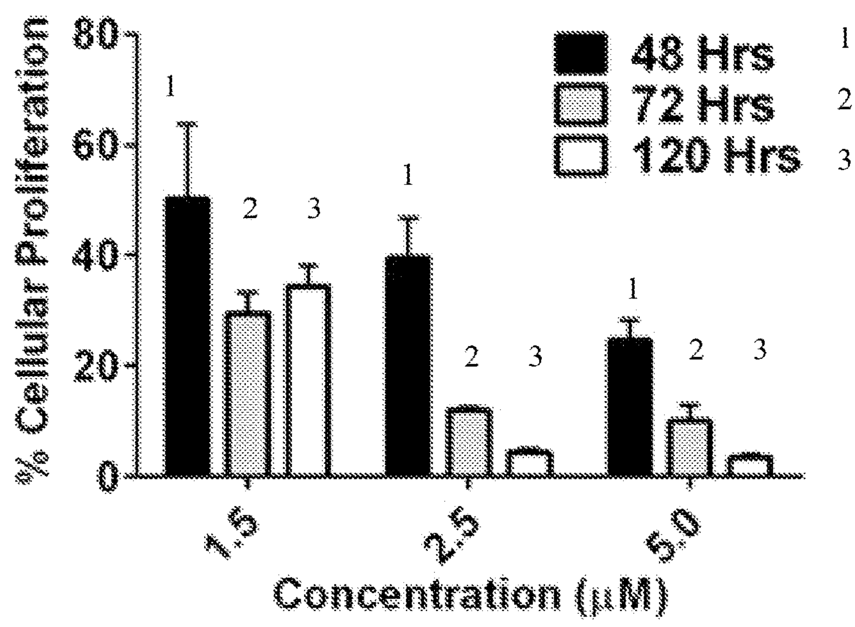
FIGS. 4A-4C demonstrate concentration dependent anti-proliferative efficacy of QA in primary bovine PASMC.
Figure 4B:
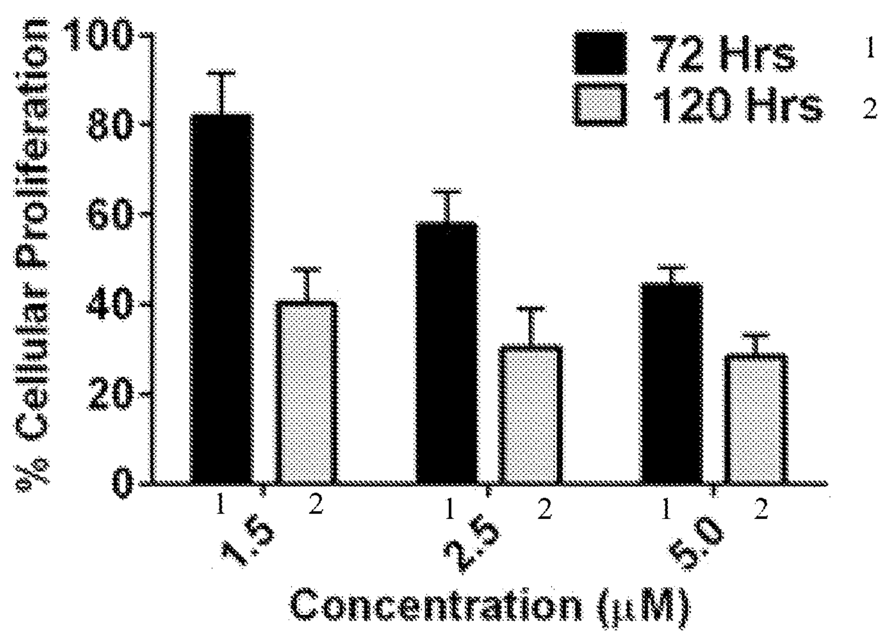
Figure 4C:
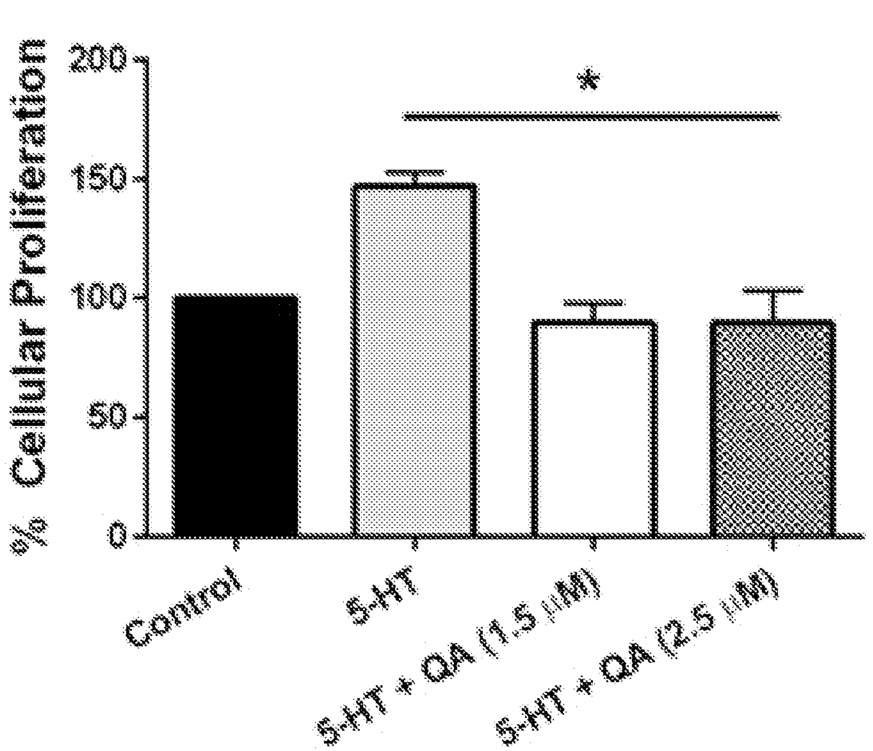

In-vitro studies to measure anti-proliferative activity of QA against pulmonary hypertension were performed using primary human PASMC (FIG. 3), primary bovine PASMC (FIG. 4) and high altitude PASMC (HAPASMC) (FIG. 4). HAPASMC, due to prolonged hypoxia exposure, are known to be hyper-proliferative in regular culture conditions, while hyper-proliferation was induced in PASMC cells by 24 hour serum starvation, or by exposure to 5-hydroxytryptamine (5-HT). Results showed that QA significantly inhibits proliferation of pulmonary artery smooth muscle cells in all tested models, i.e., primary human PASMC (FIG. 3A), serum-starved human PASMC (FIG. 3B), inherently highly proliferating bovine HAPASMC (FIG. 4A), serum-starved bovine PASMC (FIG. 4B), and 5-HT induced bovine PASMC (FIG. 4C) at sub-micromolar concentrations (1.5-5.0 μM) in a time- and concentration-dependent manner. As hyper-proliferation of vascular smooth muscle cells is one of the primary underlying causes for clinical progression of PH pathogenesis, these experiments highlight the therapeutic potential of QA in reversing PH symptoms and progression at non-toxic doses.

These results demonstrate that compositions including quinacrine are useful in methods for preventing, ameliorating or treating pulmonary hypertension and/or reducing the severity of one or more risk factors, signs, or symptoms associated with pulmonary hypertension.

Example 3: OA Inherently Internalizes in PASMC and Induces Apoptosis

Figure 5:
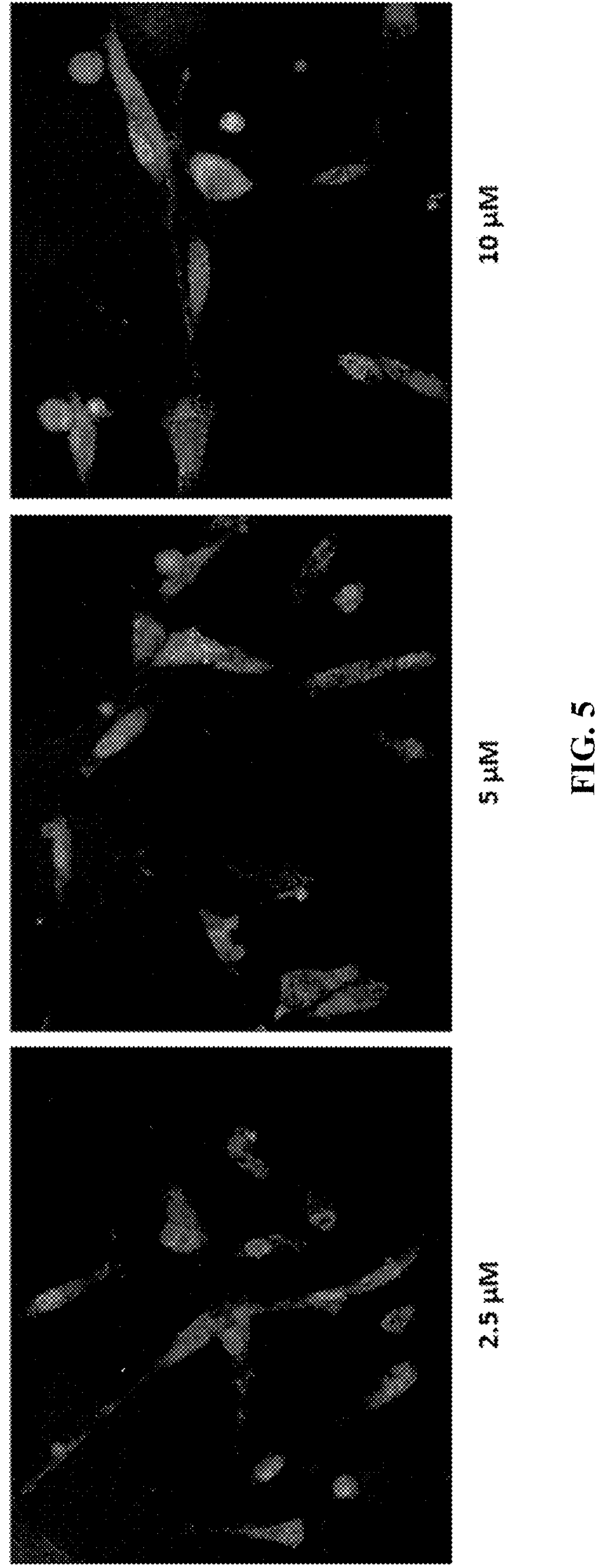
FIG. 5 demonstrates the cellular uptake of QA in primary human PASMCs as determined by fluorescence microscopy.

Cellular uptake of QA in primary human PASMC was examined. Cells were seeded in 8-chambered cover glass; and were treated with QA (2.5-10 μM) for 3 hours. After treatment, cells were fixed and imaged using EVOS-FL fluorescence microscope. It was observed that QA (green fluorescence) was capable of inherently internalizing in primary human PASMC in a concentration-dependent manner (FIG. 5).

Figure 6A:
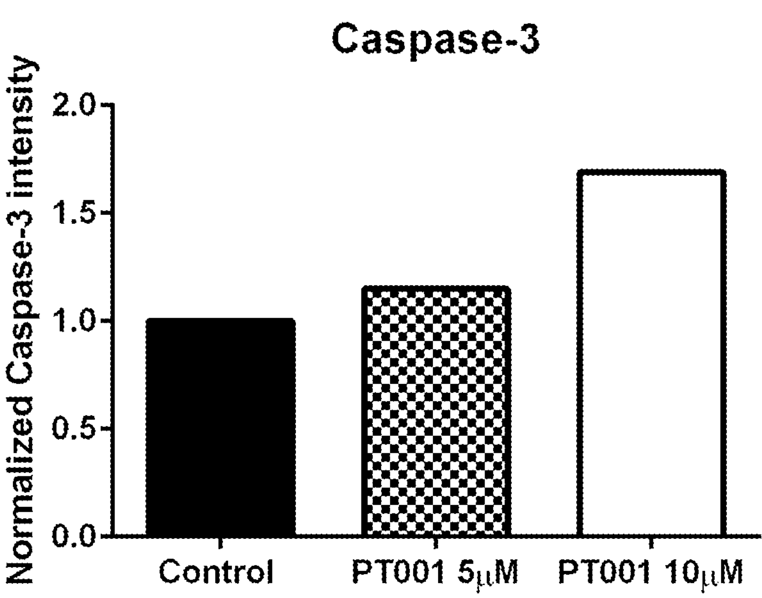
FIGS. 6A-6B demonstrate the impact of QA on cellular apoptosis in primary human PASMC.
Figure 6B:
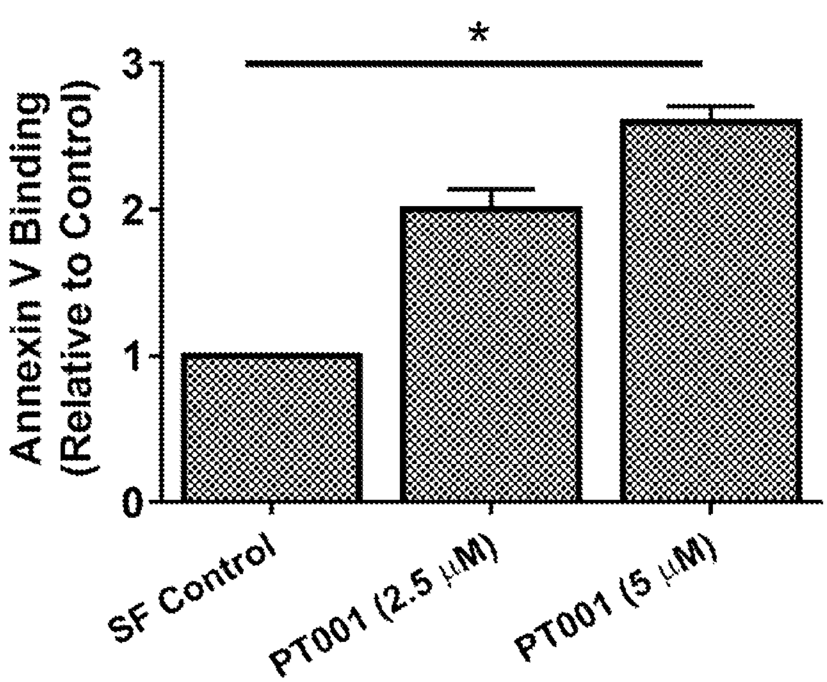

An apoptotic induction assay, i.e., Caspase-3 assay was performed to understand QA's impact on cellular apoptosis in primary human PASMCs following 6-hour treatment. It was observed that QA increased caspase-3 levels in the PASMCs in a concentration-dependent manner, thus validating the hypothesis of QA's apoptotic induction being one of the primary mechanisms of action (FIG. 6A). Moreover, another apoptotic induction assay, i.e., Annexin V FITC assay was also used to measure the effects of QA on serum-starved bovine PASMCs. Similarly, QA treatment significantly enhanced apoptotic induction as measured by fluorescence intensity of Annexin-V stained cells, in a concentration-dependent manner (FIG. 6B).

These results demonstrate that compositions including quinacrine are useful in methods for preventing, ameliorating or treating pulmonary hypertension and/or reducing the severity of one or more risk factors, signs, or symptoms associated with pulmonary hypertension.

Example 4: QA Inhibits Autophagy Process in Bovine PASMCs

Figure 7A:
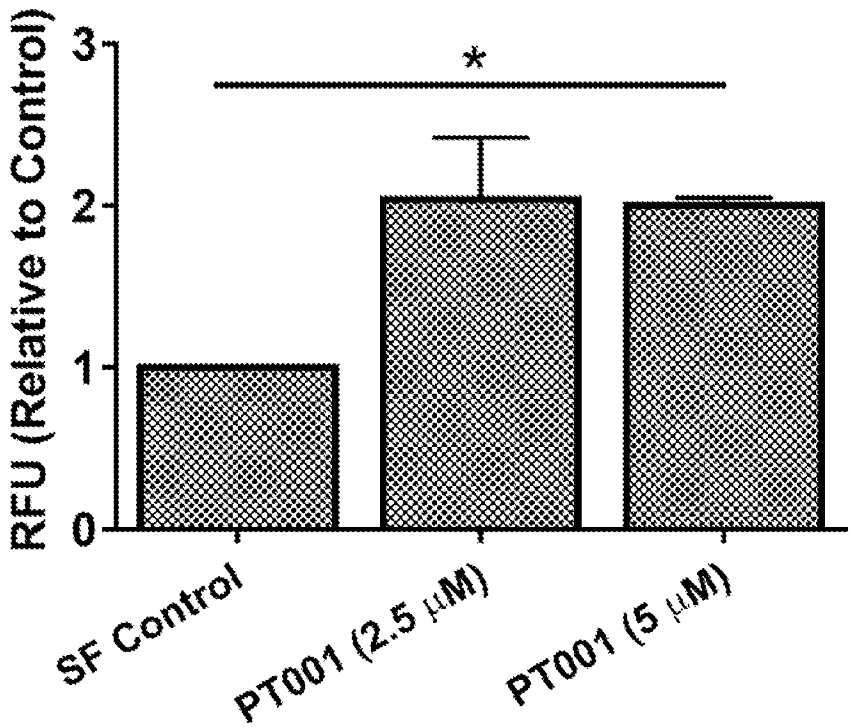
FIGS. 7A-7B demonstrate the impact of QA on the autophagy process in primary bovine PASMCs.
Figure 7B:
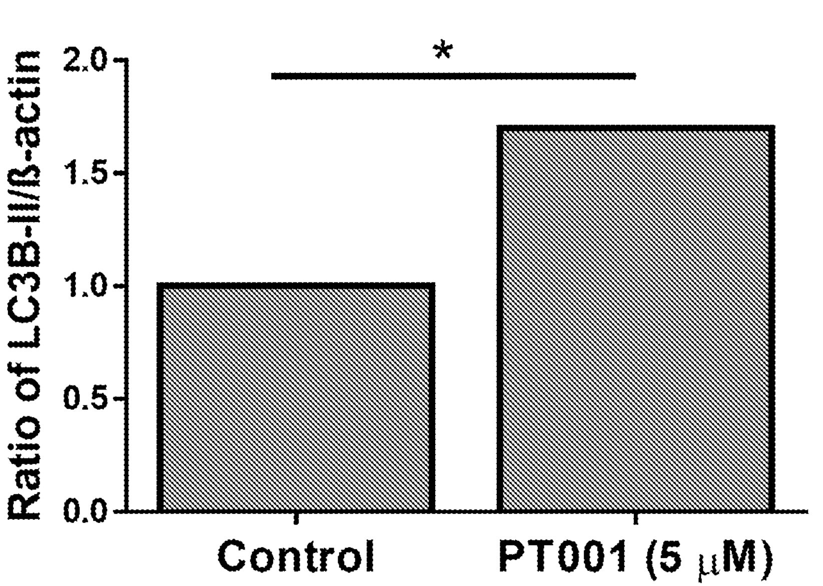
Figures 9A, 9B, 9C:
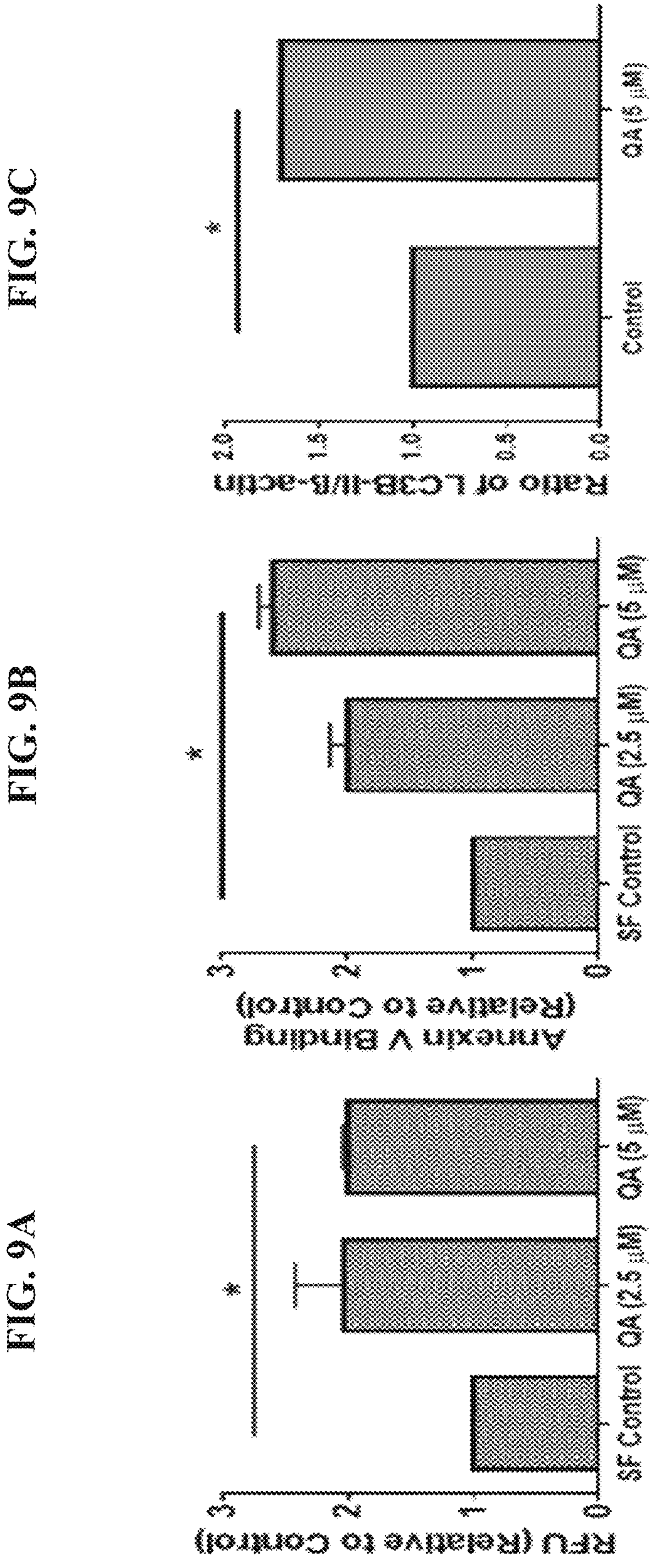
FIGS. 9A-9C demonstrate in vitro efficacy of QA in modulating apoptotic and lysosomal degradation pathways.

Autophagy inhibition (lysosomal fusion with autophagosomes) by QA was examined. Bovine PASMCs were serum starved in FBS-free media for 24 hours, and then treated with QA (2.5 and 5 μM) for 24 hours. Autophagic inhibition was measured with Cyto-ID® autophagy detection kit. As shown in FIG. 7A, QA treatment significantly enhanced the accumulation of the fluorescent dye in the autophagosomes, and thus inhibited the autophagy process by inhibiting the fusion of lysosomes with autophagosomes. QA-induced autophagy inhibition by targeting LC3B-II expression was examined using HAPASMCs. It was observed that QA treated high altitude PASMC cell lysate revealed a >2-fold increase in LC3B-II expression which is significant due to ability of bovine HAPASMC cells to mimic PAH associated hyper-proliferation (FIG. 7B, FIG. 9C).

In other independent experiments, QA's ability to modulate autophagy/apoptotic pathways was quantified in vitro in serum-starved bovine PASMC cells. Similar results were observed. As shown in FIG. 9A, QA treatment significantly enhanced accumulation of the fluorescent dye in autophagosomes, and thus inhibited the autophagy process by inhibiting fusion of lysosomes with autophagosomes. QA treatment also significantly enhanced apoptotic induction (as measured by fluorescence intensity of Annexin V FITC stained cells) in a concentration dependent manner (FIG. 9B).

Figure 8:
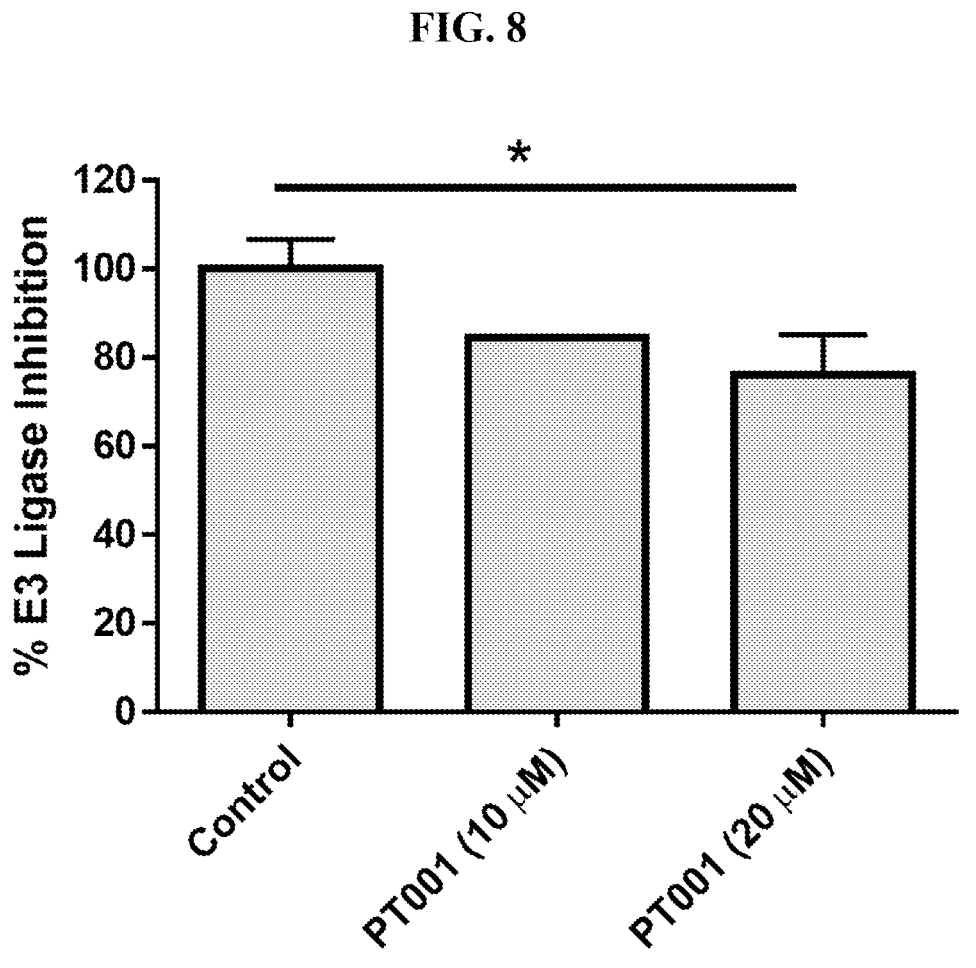

To evaluate the ability of QA to directly inhibit ITCH/AIP4 E3 ligand activity, a ubiquitin ELISA kit was used to quantify QA's ability to inhibit the ligand activity in presence of ubiquitin at multiple concentrations. QA demonstrated a dose-dependent ability to decrease overall polyubiquitination by the ITCH/AIP4 E3 ligase, with the 20 μM dose resulting in ~25% reduction in total polyubiquitination resulting from ITCH/AIP4 activity (FIG. 8).

These results demonstrate that compositions including quinacrine are useful in methods for preventing, ameliorating or treating pulmonary hypertension and/or reducing the severity of one or more risk factors, signs, or symptoms associated with pulmonary hypertension.

Figure 10A:
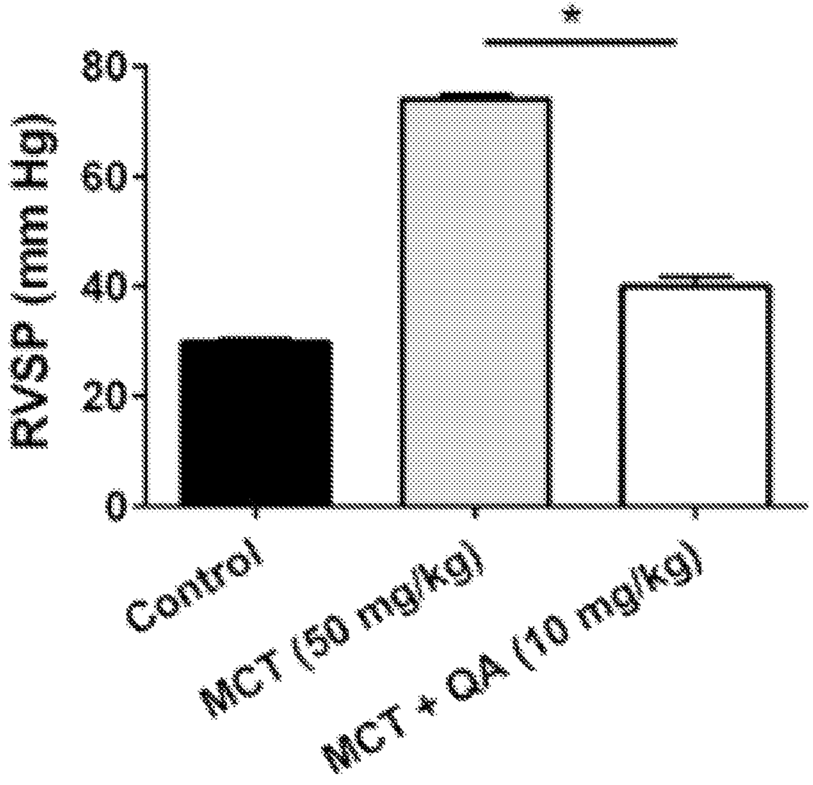
FIGS. 10A-10B demonstrate in vivo efficacy of QA in monocrotaline (MCT) induced therapeutic rat model of pulmonary hypertension (PH). Adult male SD rats were injected with MCT (50 mg/kg) by subcutaneous injection. QA administration was initiated 21 days (3 weeks) after MCT administration, once-a-day by subcutaneous route at 10 mg/kg for 10 days.
Figure 10B:
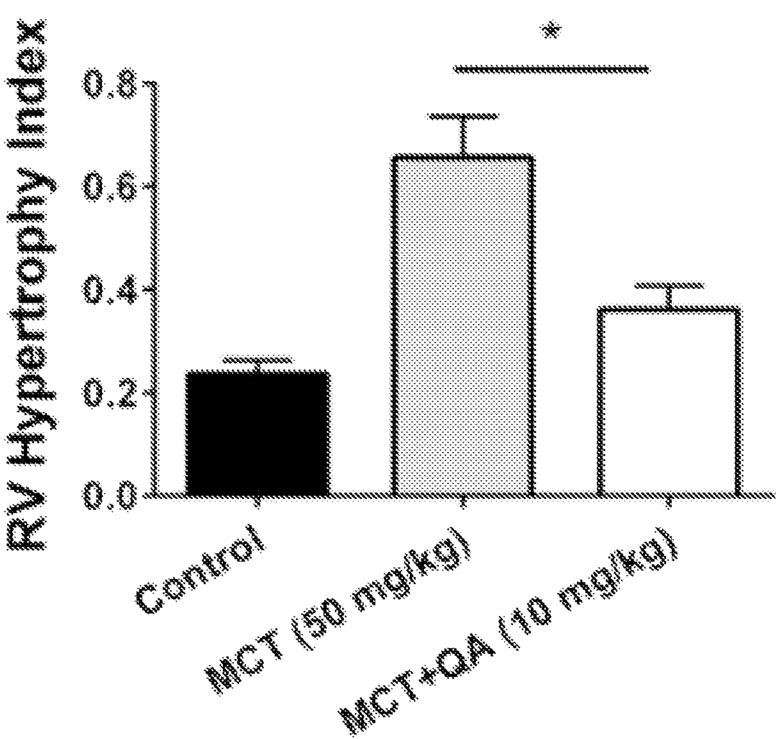

Example 5: QA Ameliorates Established Disease Symptoms and Protects Against Disease Progression in Monocrotaline (MCT) Induced Therapeutic Rodent Model of PH To determine the therapeutic activity of QA against PH, the drug was tested using chronic hemodynamic studies in a monocrotaline (MCT)-induced rodent model of pulmonary hypertension. MCT induction is a well established preliminary model, with a single subcutaneous injection of MCT producing chronic PH-like symptoms in rats over a course of 3-4 weeks. Briefly, MCT was subcutaneously injected in adult male Sprague Dawley (SD) rats at 50 mg/kg, and rats were housed for 3 weeks with free access to food and water. Following 3 weeks, once-a-day quinacrine subcutaneous injections were started at 10 mg/kg for 10 days. At the end of day 10, animals were anesthetized to determine right ventricular systolic pressure (RVSP) by RV catheterization, and RV hypertrophy (RVH) was measured by collecting the heart-lung blocks. As seen in FIGS. 10A-10B, MCT administration significantly increased RVSP (74.1±0.7 mm Hg as compared to 29.8±0.6 mm Hg in control animals). QA administration significantly reduced RVSP to 39.9±1.8 mm Hg (FIG. 10A) underscoring its efficacy in providing protection against PH progression. QA administration also significantly reduced RV hypertrophy (RVH) index from 0.66±0.08 (MCT alone) to 0.36±0.05 (QA treated animals) (FIG. 10B) which is a marker of decreased workload and proliferation of the right ventricle due to vasodilation in pulmonary arteries. These findings were unexpected given that quinacrine has never been shown to possess any vasodilatory properties, which suggests a possible novel anti-PH mechanism associated with its efficacy.

Figure 11:
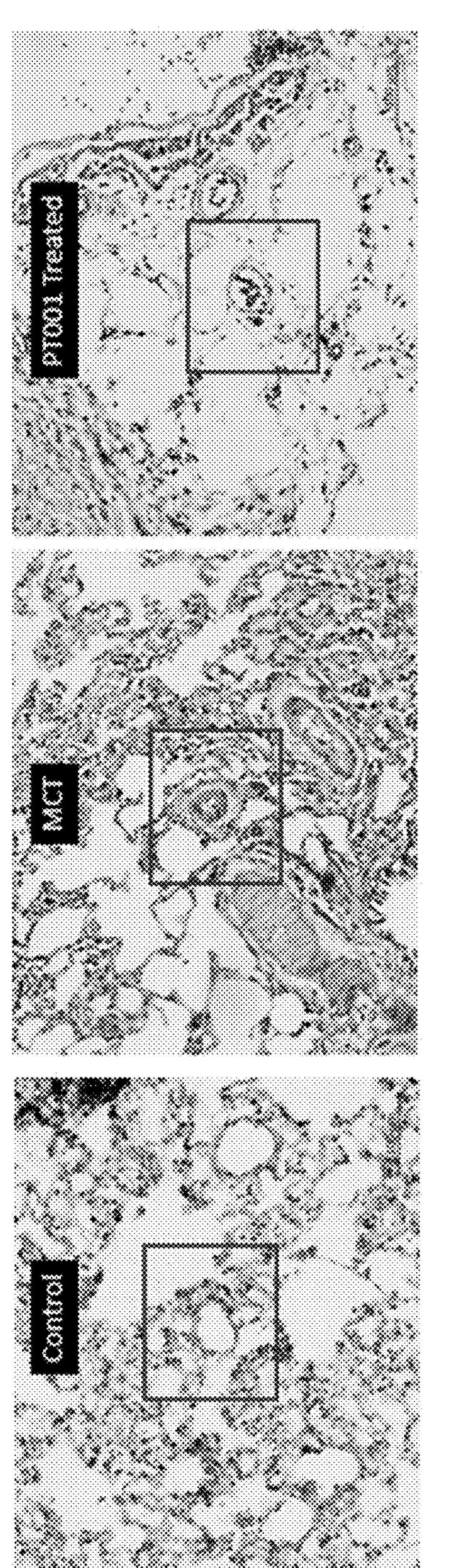
FIG. 11 demonstrates trichrome staining of lung sections of monocrotaline (MCT)-induced PAH animal model.
Figure 11:
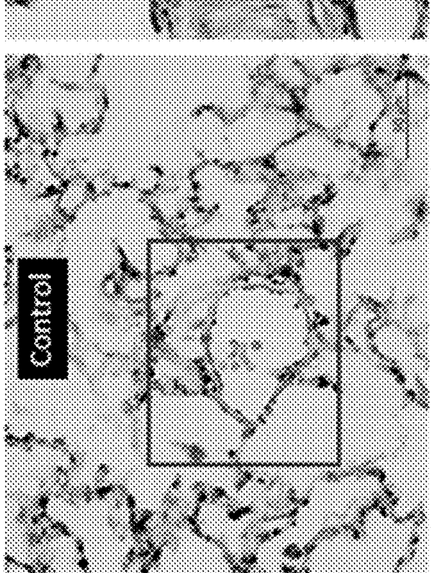

Additionally, lung tissue sections from the MCT-induced PAH lung tissue were examined using trichrome staining. Microscopic images of stained samples clearly demonstrate excessive collagen deposition and muscular wall formation in pulmonary arterioles with MCT treatment (FIG. 11; presented in red boxes). With QA treatment, significant reduction is observed in collagen and muscular deposition in pulmonary arterioles (FIG. 11), which in turn reflects in reduced pulmonary arterial pressure measured hemodynamically.

Figure 12A:
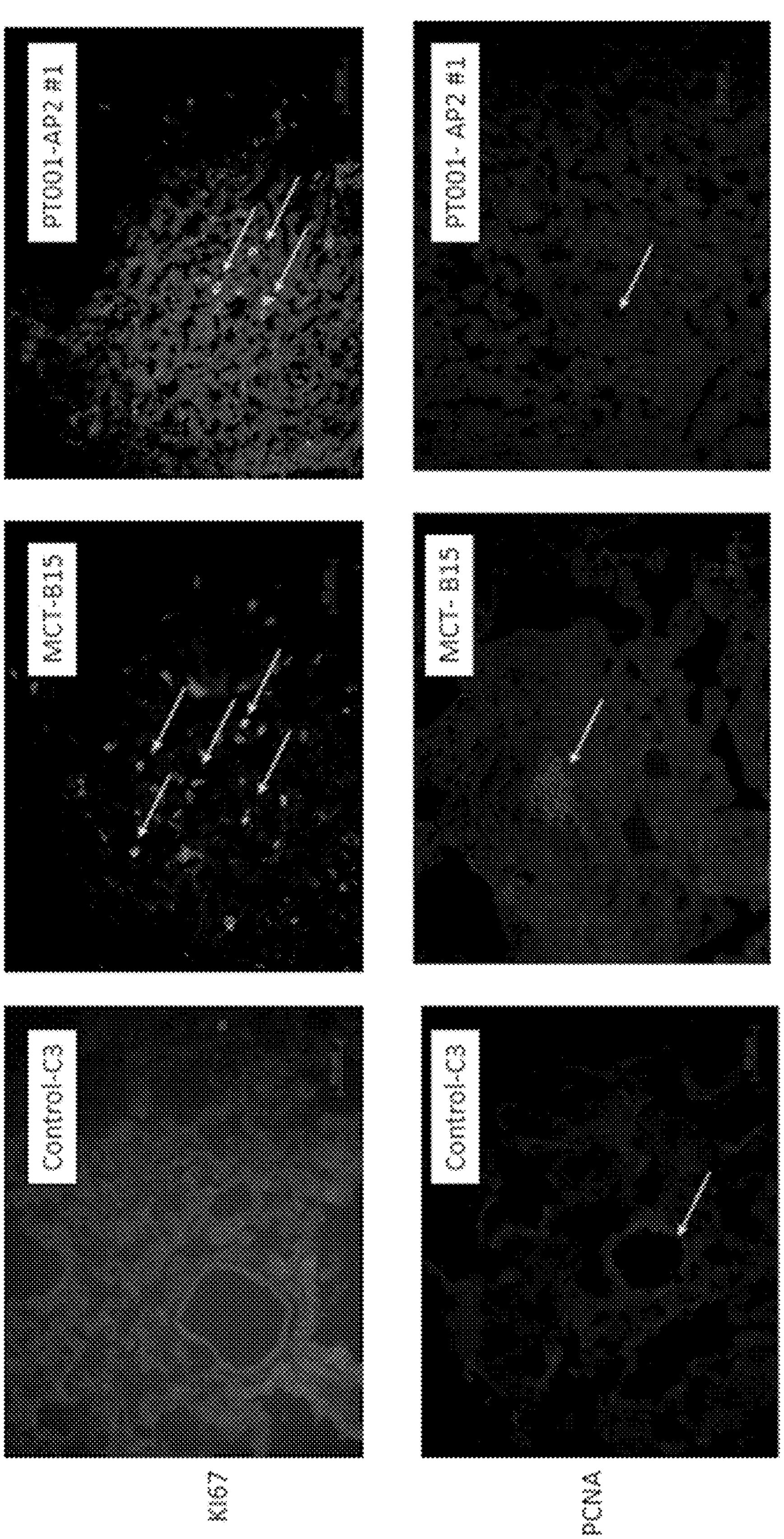
FIGS. 12A-12B show immunofluorescence imaging for MCT-induced PAH animal lung tissue slides.
Figure 12B:
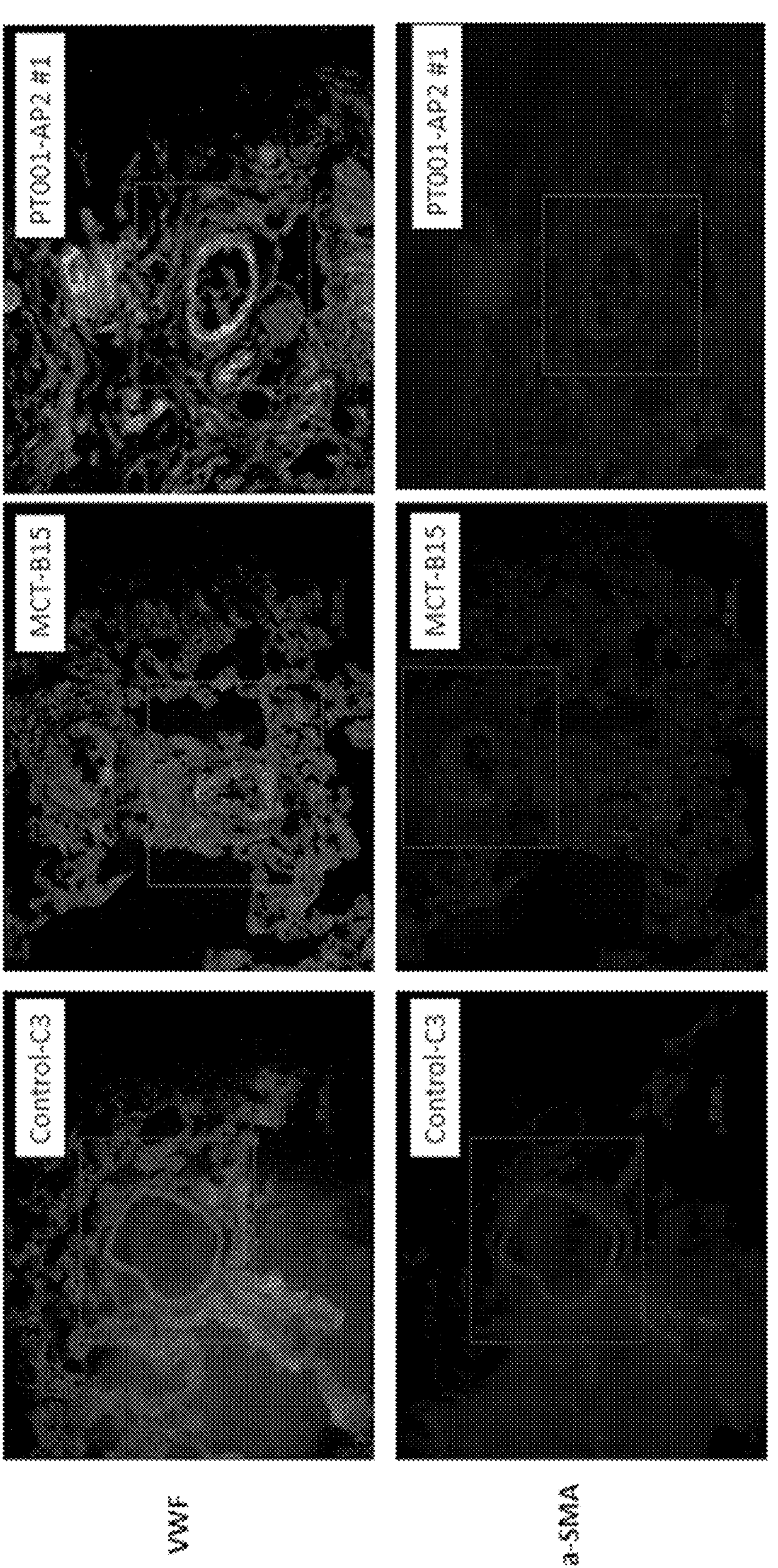

Immunofluorescence imaging of the MCT-induced PAH animal lung tissue slides was also performed. As shown in FIG. 12A, QA treated animals showed reduction in expression of Ki67 and PCNA (Proliferating Cell Nuclear Antigen), two of the hyper-proliferation markers frequently observed to be over-expressed in PAH animal models. On the other hand, QA treated animals did not show any reduction in expression of vWF (Von-Willebrand factor), or α-smooth muscle actin (α-SMA), as compared to control (FIG. 12B). Interestingly, expression of vWF and α-SMA also did not change in MCT-induced PAH animals (FIG. 12B).

Figure 13:
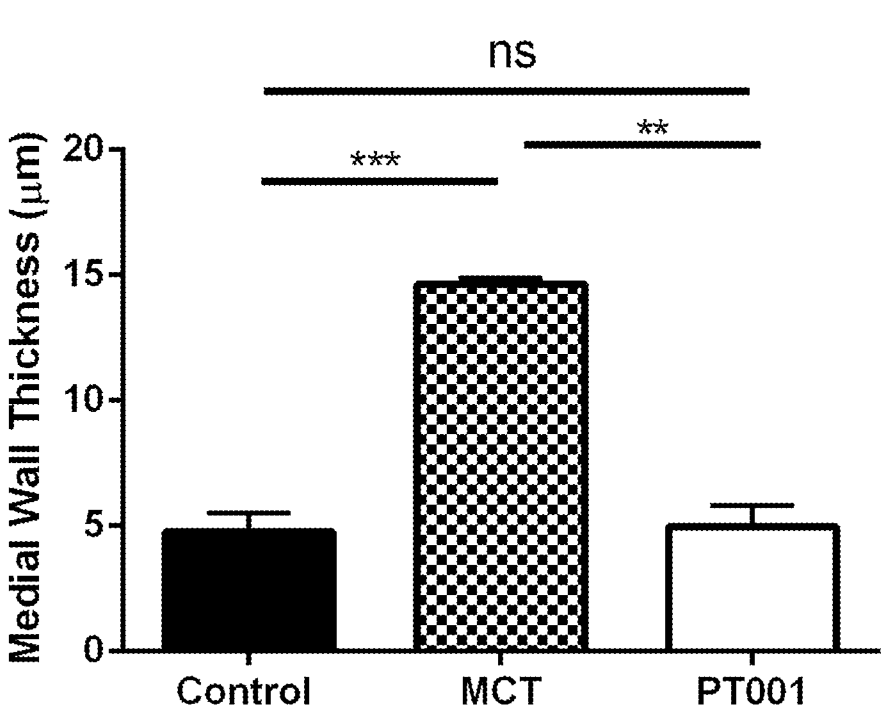
FIG. 13 demonstrates the effects of QA on medial wall thickness of pulmonary arteries in an MCT-induced PAH animal model. Significant increase in medial wall thickness of pulmonary arteries was seen in MCT-induced PAH animal tissue sections (>3-fold increase), which was attenuated by QA treatment, bringing the wall thickness back to almost normal, compared to control animals.

Medial wall thickness of pulmonary arteries was measured using the trichrome stained microscopic images. Significant increase in medial wall thickness of pulmonary arteries was seen in MCT-induced PAH animal tissue sections (>3-fold increase), which was attenuated by QA treatment, bringing the wall thickness back to almost normal, compared to sham control animals (FIG. 13).

These results demonstrate that compositions including quinacrine are useful in methods for preventing, ameliorating or treating pulmonary hypertension and/or reducing the severity of one or more risk factors, signs, or symptoms associated with pulmonary hypertension.

Figure 14A:
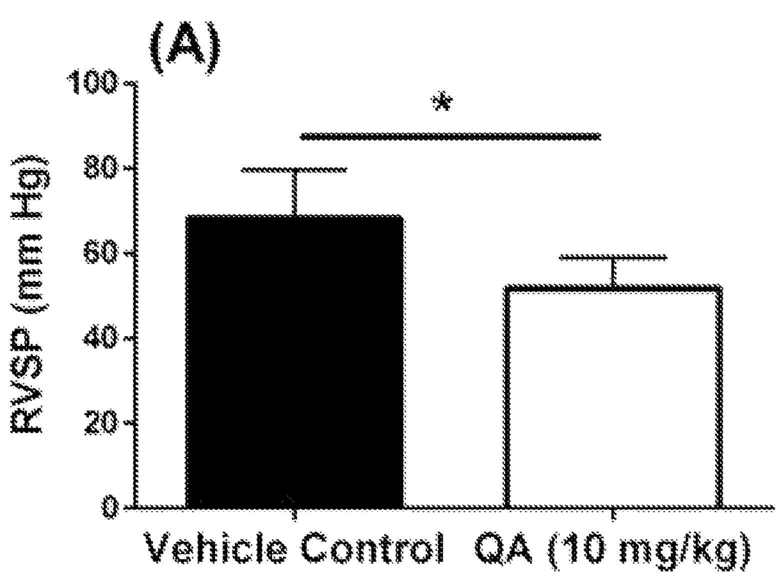
FIGS. 14A-14D demonstrate in vivo efficacy of QA in SU5416/hypoxia induced rat model of pulmonary hypertension. Adult male rats were injected with SU5416 (20 mg/kg) subcutaneously and were kept under hypoxia (10% $O_2$) for 3 weeks. QA was administered once-a-day intraperitoneally at a dose of 10 mg/kg for 21 days starting from Day 1.
Figure 14B:
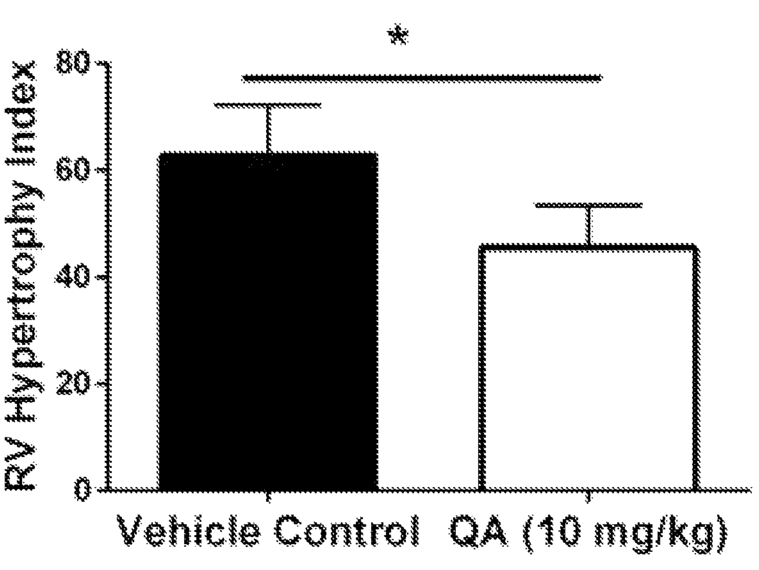
Figure 14C:
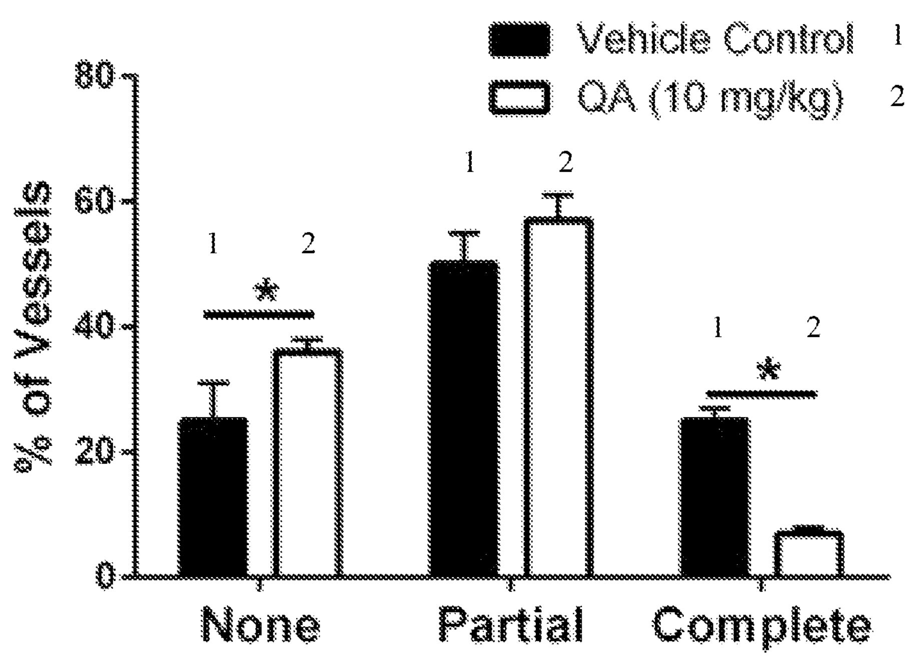
Figure 14D:
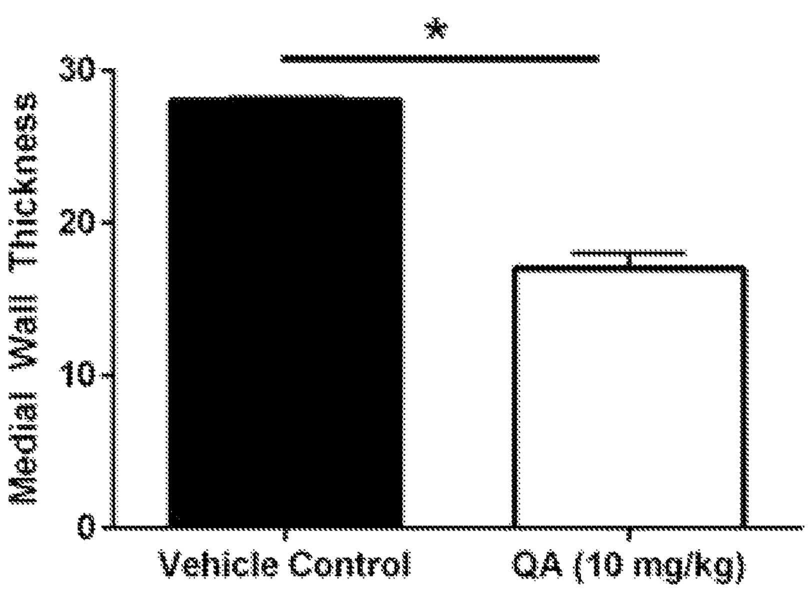

Example 6: QA Protects Against Development and Progression of PAH in a Preventative SU5416/Hypoxia Induced Rat Model QA was also tested in a preventative SU5416/hypoxia-induced PAH model, which showed similarly outstanding prophylactic results and minimal toxicity. As seen in FIGS. 14A-14D, animals were kept in hypoxia (10% $O_2$) after SU5416 injection, and were given 10 mg/kg QA once-a-day for 3 weeks from Day 1. After 3 weeks, hemodynamic studies were performed. QA administration resulted in significant reduction in RVSP (45.6±7.9 mmHg vs 62.8±9.5 mmHg for control; FIG. 14A); and RVH index (51.8±7.2 vs 68.3±11.4 for control; FIG. 14B). QA treatment also resulted in significant reduction in vessel muscularization (3.5 folds less completely muscularized blood vessels than control; FIG. 14C) and medial wall thickness (FIG. 14D). These data highlight the efficacy of QA in providing protection against developing of PH symptoms.

Figure 15:
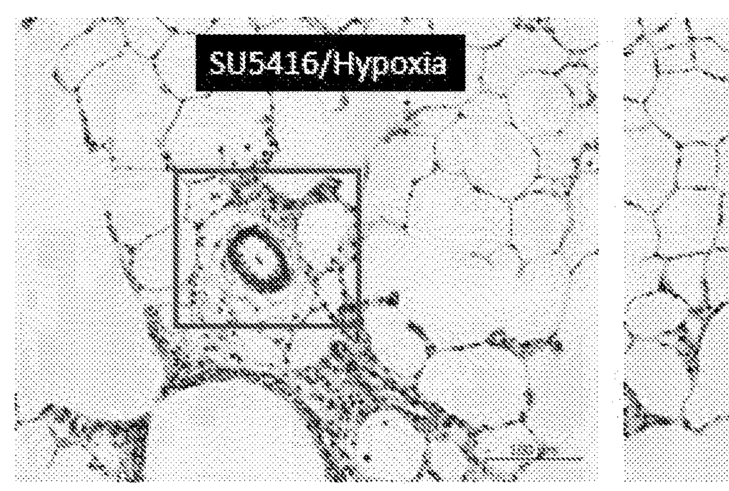
FIG. 15 demonstrates trichrome staining of lung sections of SU5416/hypoxia-induced PAH animal model.
Figure 15:
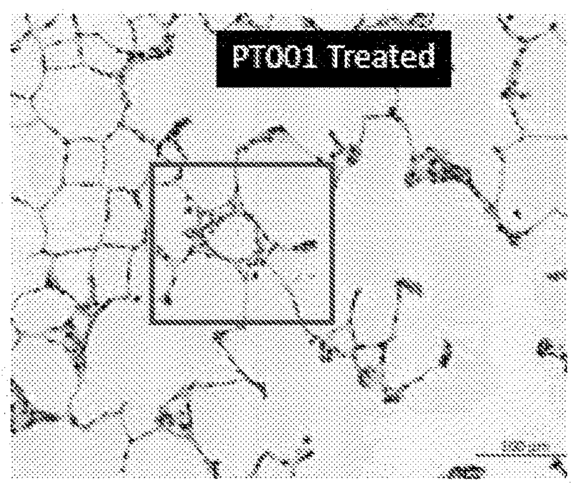
Figure 15:
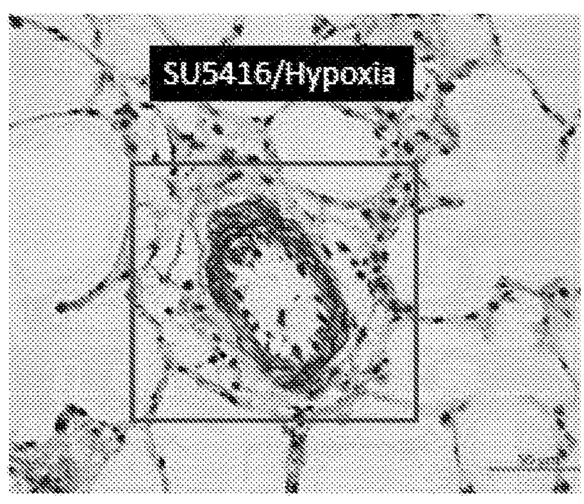
Figure 15:
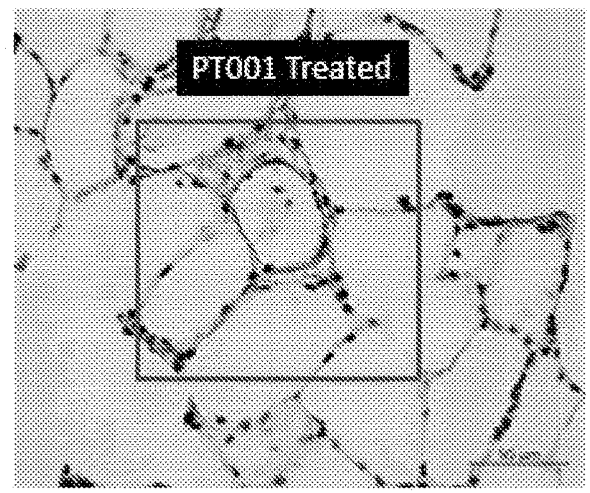

Additionally, trichrome staining clearly demonstrate excessive collagen deposition and muscular wall formation in pulmonary arterioles with SU5416/hypoxia treatment (FIG. 15; presented in red boxes). With QA treatment, significant reduction is observed in collagen and muscular deposition in pulmonary arterioles, which in turn reflects in reduced pulmonary arterial pressure measured hemodynamically.

Figure 16:
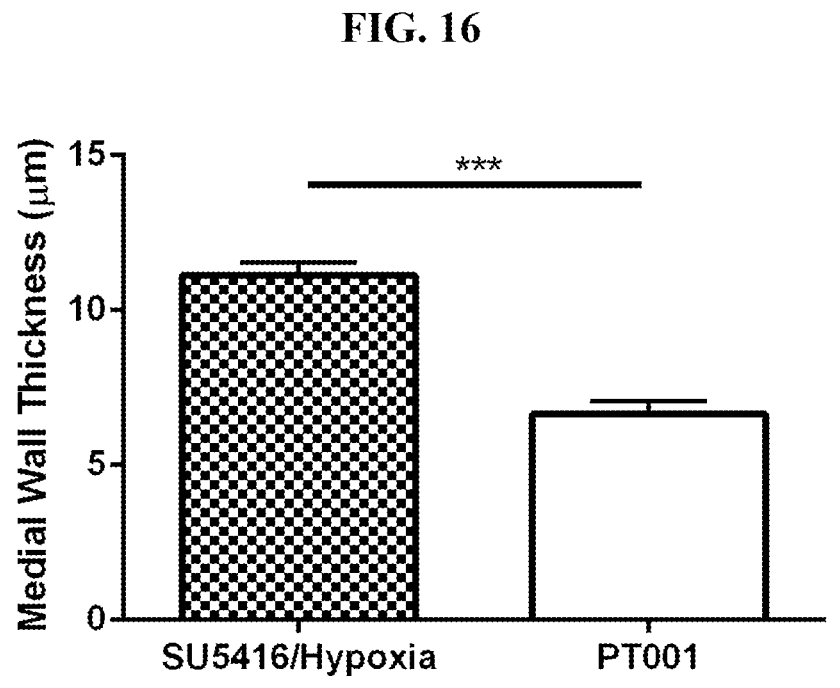

Medial wall thickness measurements demonstrated a significant reduction in medial wall thickness of pulmonary arteries in SU5416/Hypoxia-induced PAH animal tissue with QA treatment, which produced about 2-fold reduction in wall thickness as compared to SU5416/hypoxia-induced PAH animal tissue sections (FIG. 16).

Figure 17A:
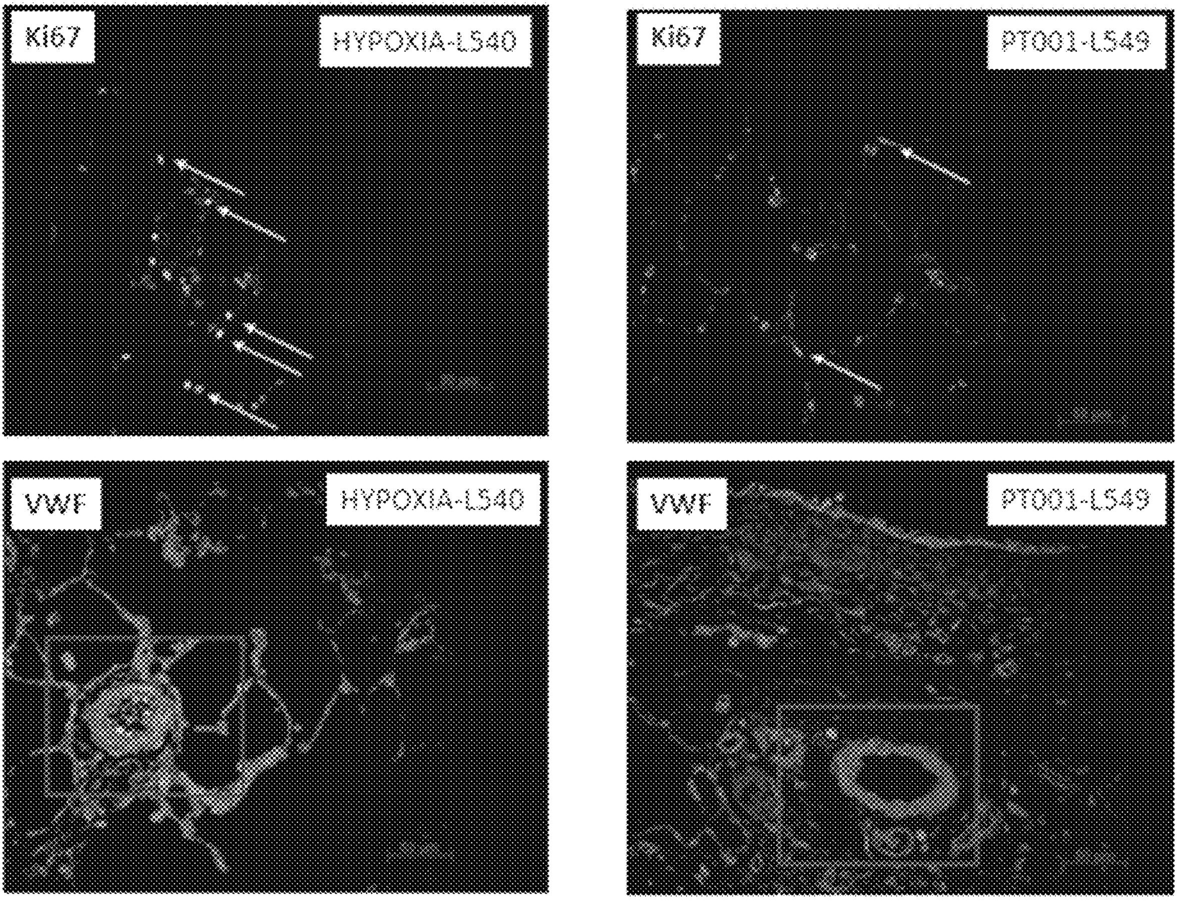
FIGS. 17A-17B demonstrate immunofluorescence imaging for SU5416/hypoxia-induced PAH animal lung tissue slides. Ki67 and PCNA exhibited reduced expression in QA treated animal as compared to control. vWF or α-SMA, exhibited no expression reduction in QA treated animal as compared to control.
Figure 17B:
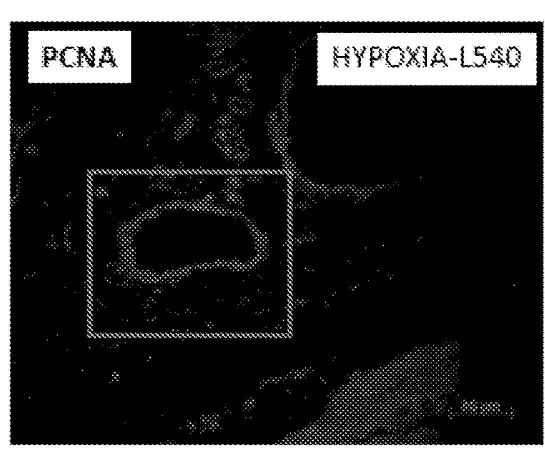
Figure 17B:
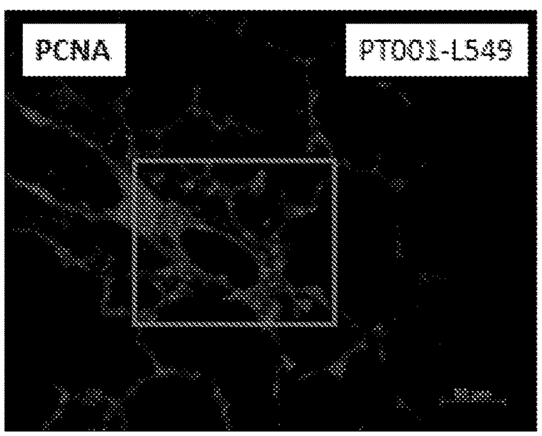
Figure 17B:
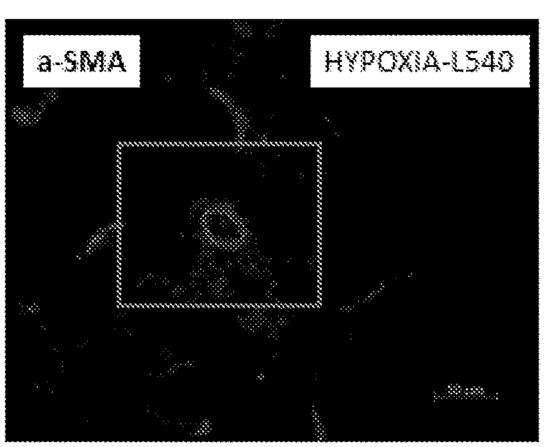
Figure 17B:
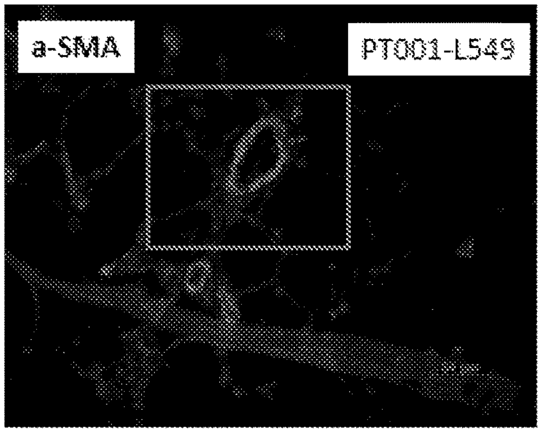

Immunofluorescence imaging of the SU5416/Hypoxia-induced PAH animal lung tissue slides demonstrates that QA treated animals showed reduction in expression of Ki67 and PCNA, while QA treated animals did not show any reduction in expression of vWF or α-SMA, as compared to SU5416/Hypoxia-treated control animals (FIGS. 17A-17B).

These results demonstrate that compositions including quinacrine are useful in methods for preventing, ameliorating or treating pulmonary hypertension and/or reducing the severity of one or more risk factors, signs, or symptoms associated with pulmonary hypertension.

Figure 18A:
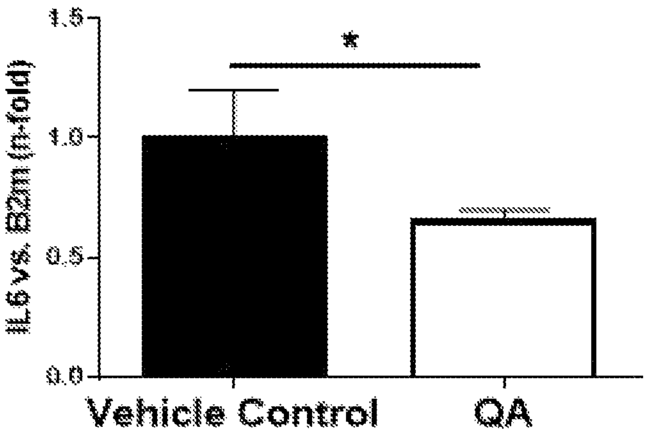
FIGS. 18A-18F demonstrate in vivo modulation of disease causing molecular pathways by QA in SU5416/hypoxia induced rat model of pulmonary arterial hypertension. QA treatment inhibited mRNA expression of inflammatory marker IL-6 (FIG. 18A), smooth muscle actin marker Acta2 (FIG. 18B), and endothelial cell proliferation marker Serpinel (FIG. 18C), but not BMPR2 activation marker Idl (FIG. 18D). mRNA levels were normalized with J2 microglobulin mRNA.
Figure 18B:
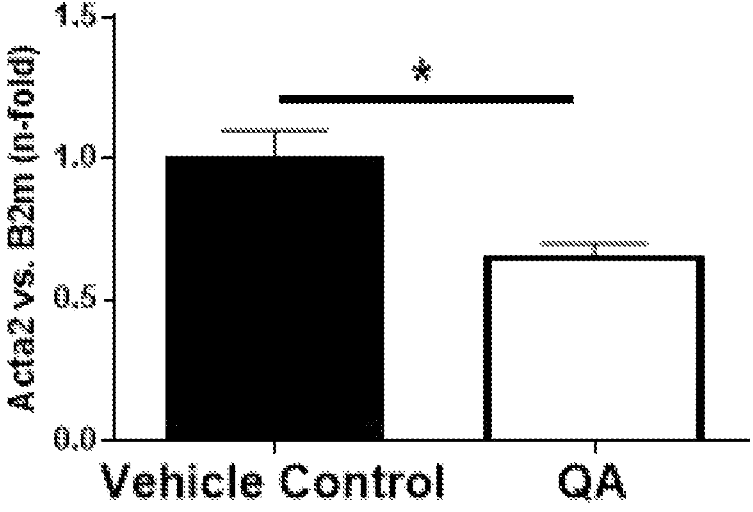
Figure 18C:
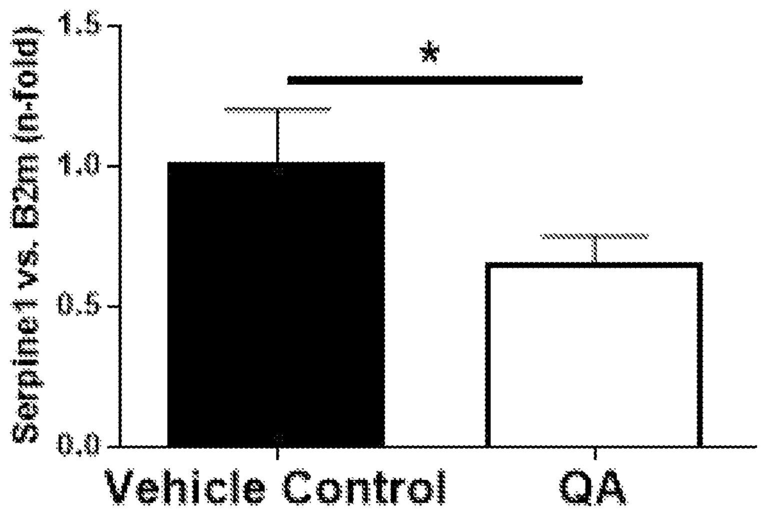
Figure 18D:
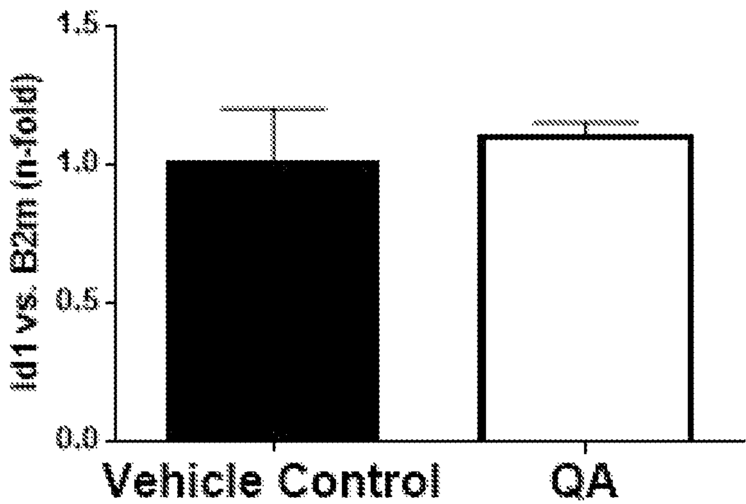

Example 7: QA Protects Against PH Proression by Modulating Multiple Disease Causing Pathways in S5416/Hypoxia Induced Rat Model To determine underlying mechanisms responsible for therapeutic effects of QA, its effect on expression of various proteins was analyzed by means of quantifying mRNA expression using real time PCR and western blot analysis (FIGS. 18A-18F). It has been reported that expression of BMPR2 is reduced in SuHx PH model, which in turn promotes expression of inflammatory cytokines. mRNA analysis revealed that IL-6 mRNA levels decreased in QA treated animals (FIG. 18A). Further, Acta2 gene (smooth muscle actin-alpha) expression decreased in QA treated animals (FIG. 18B). Serpin1 (plasminogen activator inhibitors-1) is normally overexpressed during hypoxia and involved in vascular remodeling and plexiform formation. QA treatment reduced the mRNA levels of serpinel (FIG. 18C). However, QA treatment did not significantly change Id3 mRNA level, corresponding to BMPR2 expression (FIG. 18D).

Figure 18E:
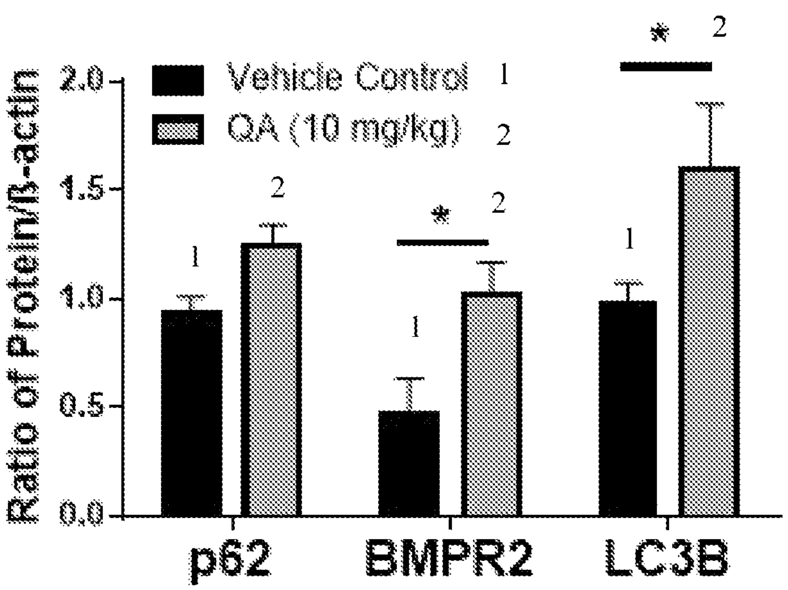
Figure 18F:
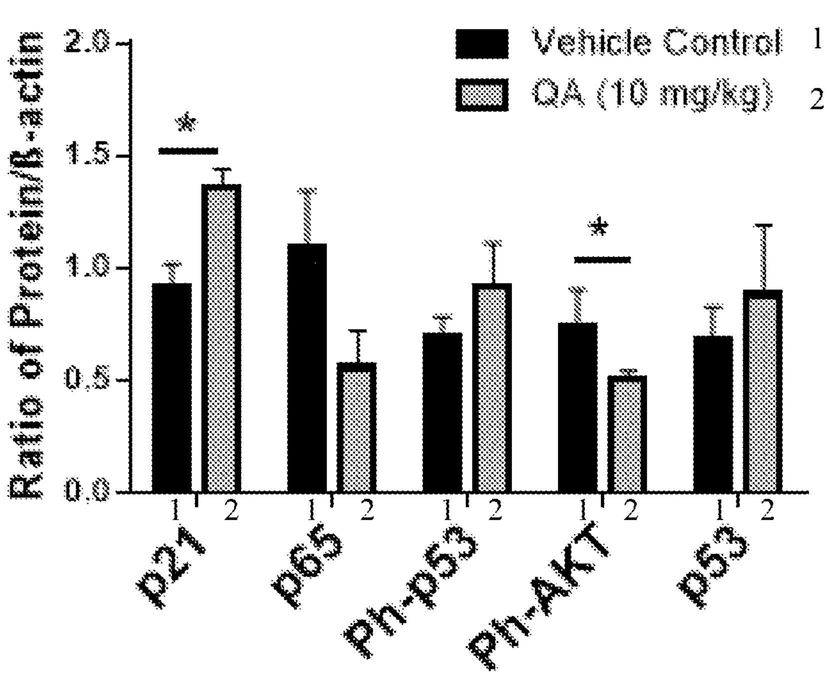

Quinacrine inhibits autophagy, and protects endogenous BMPR2 in PH lungs in-vivo. To evaluate the mechanism of therapeutic efficacy, several protein markers in right lung homogenate from SU5416/Hypoxia control as well as QA treated animals were quantified using western blotting (FIGS. 18E & 18F). It was observed that after QA treatment, autophagy markers LC3B-II and p62 were accumulated in the whole cell lysate (FIG. 18E). The accumulation of p62, a protein degraded by autophagy pathways, is indicative of autophagy inhibition. Western blot studies also revealed that QA augmented accumulation of BMPR2 by >2-fold in comparison to control animals (FIG. 18E), while mRNA analysis demonstrated no significant changes in BMPR2 mRNA expression. Taken together, these results suggest that increased BMPR2 accumulation following QA treatment may actually be a consequence of the ability of QA to block the degradation of BMPR2 protein via lysosomal pathway. This observation is significant as it points toward an alternate therapeutic strategy that differs from traditional approaches focused at improving BMPR2 expression and production in vivo. As shown in FIGS. 18D-18E, while QA does not promote BMPR2 protein production, it may safeguard endogenous BMPR2 protein from degradation, thus improving overall BMPR2 expression.

Further, the effect of QA treatment on apoptosis was observed by measuring the expression/accumulation of p21, p53 and phosphorylated-p53. QA treatment resulted in a significant increase in the expression of p21 protein in tissue lysates (FIG. 18F). Interestingly, QA treatment also produced a significant reduction in p65, a surrogate marker for NF-kB expression and a prominent inflammatory marker suggesting the role of QA's anti-inflammatory potential in its anti-PH efficacy (FIG. 18F). Expression of phospho-AKT and phospho-p65 (molecular markers of NF-kB) also decreased. These results suggest a multi-target potential of QA against PH.

These results demonstrate that compositions including quinacrine are useful in methods for preventing, ameliorating or treating pulmonary hypertension and/or reducing the severity of one or more risk factors, signs, or symptoms associated with pulmonary hypertension.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed is:

1. A method for treating pulmonary arterial hypertension, comprising administering a therapeutically effective amount of quinacrine or a pharmaceutically acceptable salt thereof to a subject in need thereof.

2. The method of claim 1, wherein the subject has been diagnosed as having pulmonary arterial hypertension.

3. The method of claim 2, wherein the method reduces one or more signs or symptoms of pulmonary arterial hypertension, wherein the signs or symptoms of pulmonary arterial hypertension comprise one or more of persistent dyspnea on exertion, chest pain, light-headedness, exertional presyncope/syncope, palpitations, fatigue, weakness, voice hoarseness due to compression of a left laryngeal nerve by a dilated pulmonary artery, venous jugular distension, hepato-jugular reflux, hepatomegaly, hepatalgia, lower limb edema, ascites, generalized edema, intimal fibrosis of pulmonary arteries, increased medial thickness of pulmonary arteries, intimal hyperplasia of muscular pulmonary arteries, pulmonary artery thrombotic lesions, pulmonary arteriolar occlusion, pulmonary vascular pruning, plexiform lesions in pulmonary arteries, increased right ventricular systolic pressure, increased right ventricular hypertrophy, or pulmonary vasculature hyper-proliferation, or wherein the subject exhibits serum or plasma brain natriuretic peptide (BNP) >180 pg/mL, or elevated serum or plasma N-terminal fragment of proBNP (NT-proBNP) ≥1400 pg/mL.

4. The method of claim 1, wherein the subject is human.

5. The method of claim 1, wherein the quinacrine or pharmaceutically acceptable salt thereof is administered orally, topically, intranasally, via inhalation, intrapleurally, systemically, intravenously, subcutaneously, intraperitoneally, intradermally, intraocularly, iontophoretically, transmucosally, or intramuscularly.

6. The method of claim 1, further comprising separately, sequentially or simultaneously administering one or more additional therapeutic agents to the subject.

7. The method of claim 6, wherein the additional therapeutic agents are selected from the group consisting of: endothelin receptor antagonists (ETRAs), guanylate cyclase stimulators, prostacyclin analogues, phosphodiesterase (PDE)-5 inhibitors, dehydroepiandrosterone (DHEA), cyclosporine, tacrolimus, bestatin, imatinib, calcium-channel blockers (CCBs), dichloroacetate (DCA), trimetazidine, ranolazine, 4-phenylbutyrate, tauroursodeoxycholic acid, and salubrinal.

8. The method of claim 1, wherein the subject exhibits a decrease in right ventricular systolic pressure (RVSP) and/or a reduction in right ventricular hypertrophy (RVH) following administration of quinacrine relative to an untreated control subject with pulmonary arterial hypertension.

9. The method of claim 1, wherein the subject exhibits a decrease in vessel muscularization and/or a reduction in medial wall thickness in pulmonary arterioles following administration of quinacrine relative to an untreated control subject with pulmonary arterial hypertension.

10. The method of claim 1, wherein the quinacrine is administered daily for 1 week, 2 weeks, 3 weeks, 4 weeks, 5 weeks, 6 weeks, 12 weeks, or throughout the subject's life.

11. The method of claim 2, wherein the pulmonary arterial hypertension is idiopathic PAH (IPAH), familial PAH (FPAH), or associated PAH (APAH).

12. The method of claim 1, wherein the subject harbors a mutation selected from the group consisting of bone morphogenetic protein receptor type II (BMPR2), Serotonin (5-HTT) transporter, and Activin-Like Kinase Type-1 Receptor (ALK-1).

13. The method of claim 1, wherein the subject is a pediatric patient, a geriatric patient, an immunocompromised patient, a female patient, or a male patient.

14. The method of claim 13, wherein the subject is of Caucasian, South Asian, Southeastern Asian, or Middle-eastern descent.

15. The method of claim 1, wherein the effective amount of quinacrine is about 1 mg/kg to about 15 mg/kg or about 1 μM to about 10 μM.

* * * * *